(12) United States Patent
Burg et al.

(10) Patent No.: US 11,229,370 B2
(45) Date of Patent: Jan. 25, 2022

(54) PORTABLE DEVICE WITH MULTIPLE INTEGRATED SENSORS FOR VITAL SIGNS SCANNING

(71) Applicant: HEALTHY.IO LTD., Tel Aviv-Jaffa (IL)

(72) Inventors: Bernard Burg, Menlo Park, CA (US); Ivo Clarysse, San Francisco, CA (US); Walter De Brouwer, Los Altos, CA (US); Brandon Woolsey, San Jose, CA (US); Avita Sirimitr, Redwood City, CA (US)

(73) Assignee: HEALTHY.IO LTD., Tel Aviv-Jaffa (IL)

( * ) Notice: Subject to any disclaimer, the term of this patent is extended or adjusted under 35 U.S.C. 154(b) by 390 days.

(21) Appl. No.: 16/293,664

(22) Filed: Mar. 6, 2019

(65) Prior Publication Data
US 2019/0298183 A1    Oct. 3, 2019

Related U.S. Application Data

(63) Continuation of application No. 14/704,961, filed on May 5, 2015, now abandoned.
(Continued)

(51) Int. Cl.
*A61B 5/00*   (2006.01)
*A61B 5/0205* (2006.01)
(Continued)

(52) U.S. Cl.
CPC .......... *A61B 5/02055* (2013.01); *A61B 5/021* (2013.01); *A61B 5/02433* (2013.01); *A61B 5/113* (2013.01); *A61B 5/1135* (2013.01); *A61B 5/14551* (2013.01); *A61B 5/14552* (2013.01); *A61B 5/282* (2021.01); *A61B 5/316* (2021.01); *A61B 5/332* (2021.01); *A61B 5/352* (2021.01);
(Continued)

(58) Field of Classification Search
None
See application file for complete search history.

(56) References Cited

U.S. PATENT DOCUMENTS 7,197,351 B2 *  3/2007  Umeda ................... A61B 5/332
                                                       600/393
7,310,550 B2 * 12/2007  Ishida .................... A61B 5/332
                                                       600/523
(Continued)

*Primary Examiner* — Shirley X Jian
(74) *Attorney, Agent, or Firm* — Finnegan, Henderson, Farabow, Garrett & Dunner, LLP

(57) ABSTRACT

In one embodiment of the invention, a portable device with multiple integrated sensors for vital signs scanning and method of using said device is disclosed. The portable personal scanning device includes multiple sensors such as a plurality of ECG, thermometer, PPG, accelerometer, and microphone for determining a user's vital signs. The method includes concurrently scanning with one or more sensors, validating and enhancing the results of each sensor scan with other concurrent sensor scan and patient interaction models, processing the sensor scans separately or in combination to extract user's vital signs, validating the vital signs extracted by comparison to physiological models, and fusing the similar vital signs extracted from more than one process according to a determination of the measure of quality of the process that produced the vital sign.

8 Claims, 32 Drawing Sheets

Related U.S. Application Data

(60) Provisional application No. 61/988,889, filed on May 5, 2014.

(51) Int. Cl.
| | | |
|---|---|---|
| *A61B 5/113* | (2006.01) | |
| *A61B 5/1455* | (2006.01) | |
| *A61B 7/04* | (2006.01) | |
| *A61B 5/024* | (2006.01) | |
| *A61B 7/00* | (2006.01) | |
| *A61B 5/021* | (2006.01) | |
| *A61B 5/282* | (2021.01) | |
| *A61B 5/316* | (2021.01) | |
| *A61B 5/332* | (2021.01) | |
| *A61B 5/352* | (2021.01) | |
| *A61B 5/01* | (2006.01) | |
| *A61B 5/08* | (2006.01) | |

(52) U.S. Cl.
CPC .......... *A61B 5/6814* (2013.01); *A61B 5/6826* (2013.01); *A61B 5/721* (2013.01); *A61B 5/725* (2013.01); *A61B 5/7221* (2013.01); *A61B 5/7246* (2013.01); *A61B 5/7257* (2013.01); *A61B 7/003* (2013.01); *A61B 7/04* (2013.01); *A61B 5/01* (2013.01); *A61B 5/0816* (2013.01); *A61B 2560/0462* (2013.01); *A61B 2560/0475* (2013.01); *A61B 2562/0219* (2013.01)

(56) References Cited

U.S. PATENT DOCUMENTS

| | | | | |
|---|---|---|---|---|
| 8,244,336 | B2* | 8/2012 | Wang | A61B 5/332 |
| | | | | 600/509 |
| 9,110,498 | B2* | 8/2015 | Martinez | F16M 13/04 |
| 11,090,003 | B2* | 8/2021 | Zhao | A61B 5/7221 |
| 2003/0097078 | A1* | 5/2003 | Maeda | A61B 5/339 |
| | | | | 600/509 |
| 2011/0295083 | A1* | 12/2011 | Doelling | A61B 5/11 |
| | | | | 600/301 |
| 2013/0171599 | A1* | 7/2013 | Bleich | A61B 5/486 |
| | | | | 434/247 |
| 2014/0180019 | A1* | 6/2014 | Martinez | A61B 5/681 |
| | | | | 600/301 |
| 2014/0228649 | A1* | 8/2014 | Rayner | G16H 20/30 |
| | | | | 600/301 |

\* cited by examiner

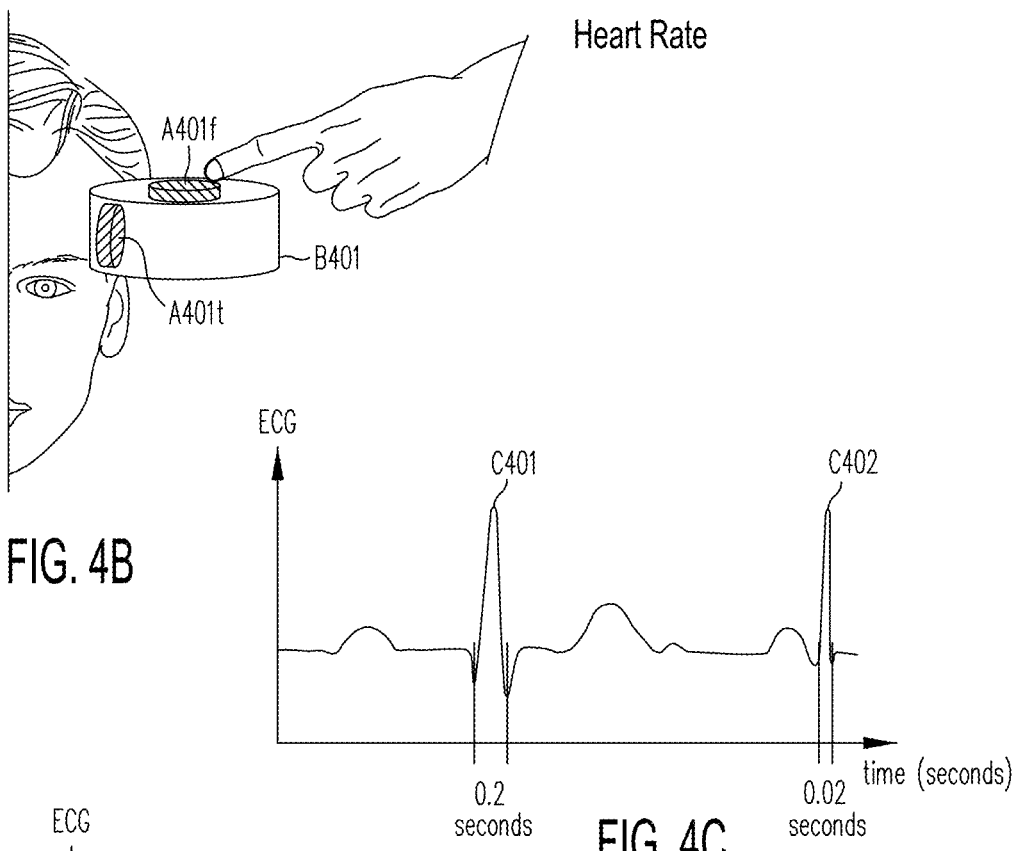
FIG. 4B
FIG. 4C
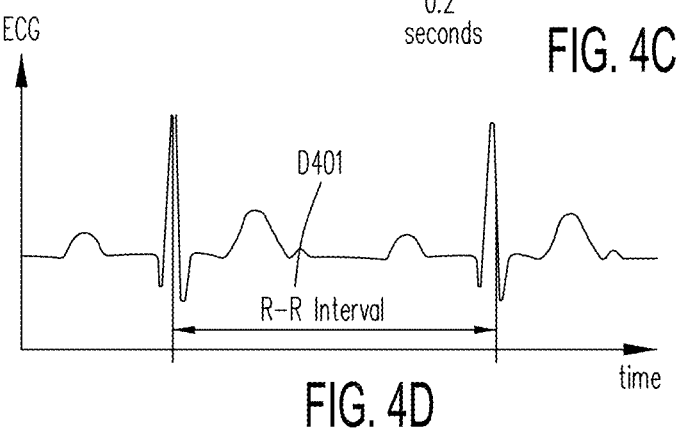
FIG. 4D
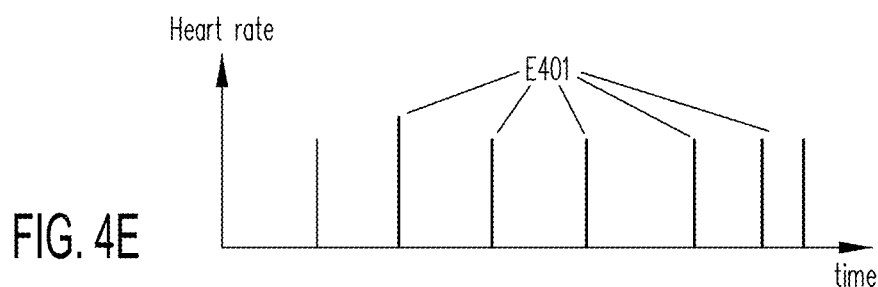
FIG. 4E

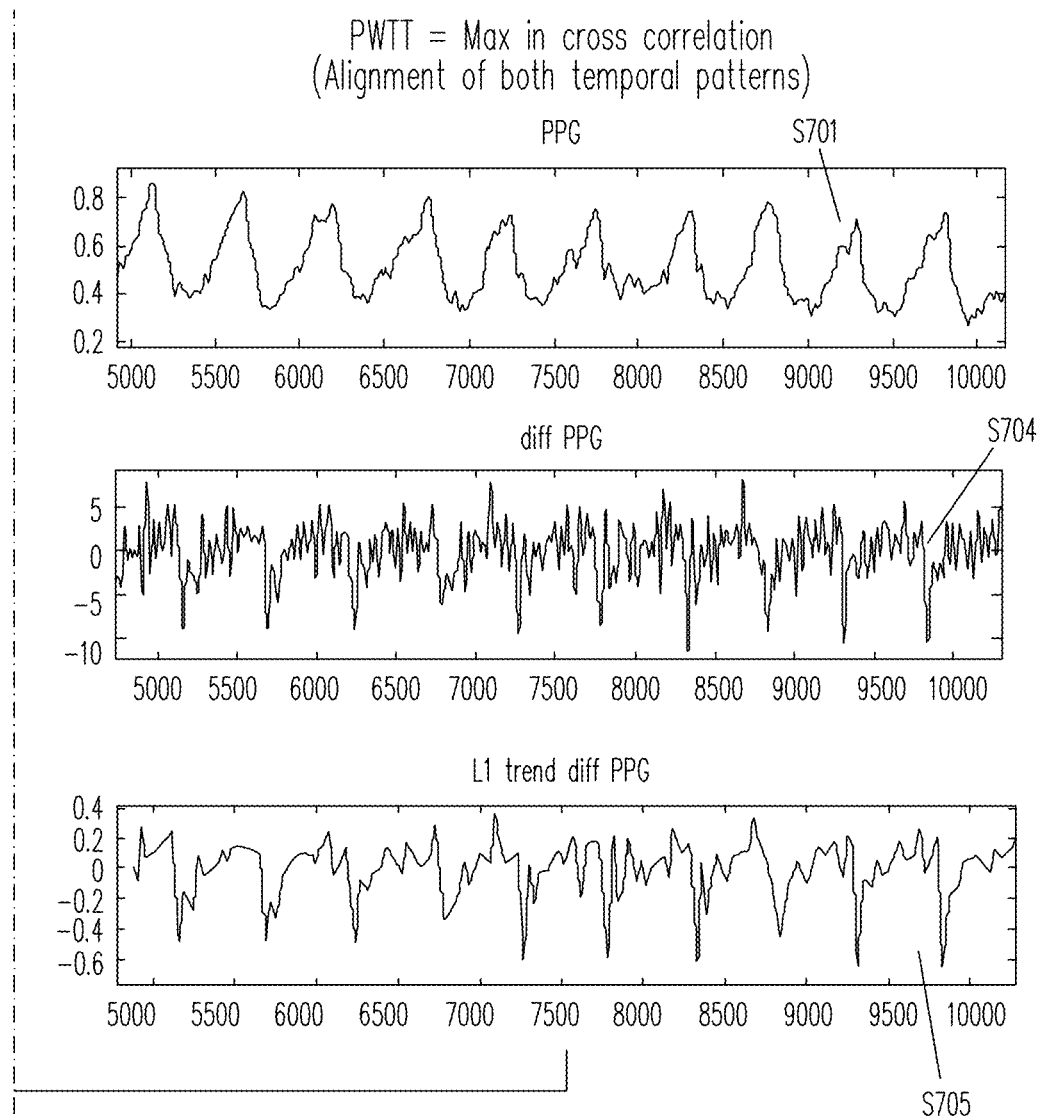
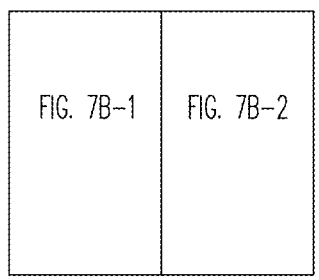
FIG. 7B-2
KEY TO
FIG. 7B

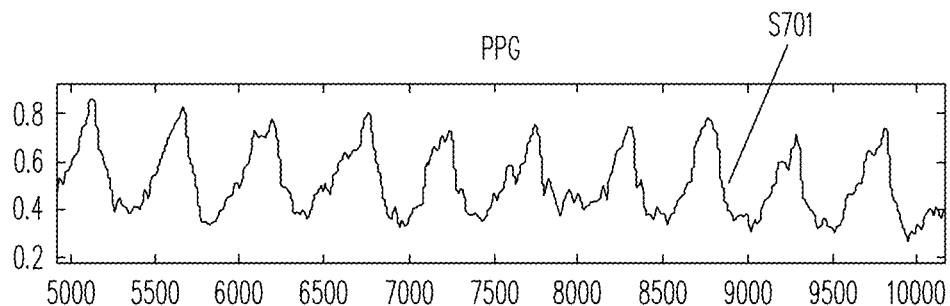
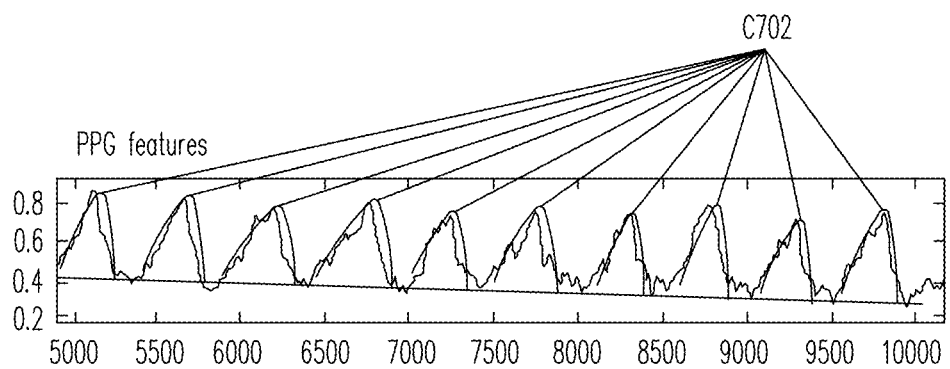
FIG. 7C-2
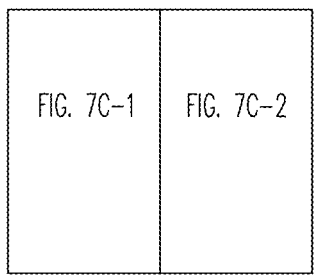
KEY TO
FIG. 7C

KEY TO

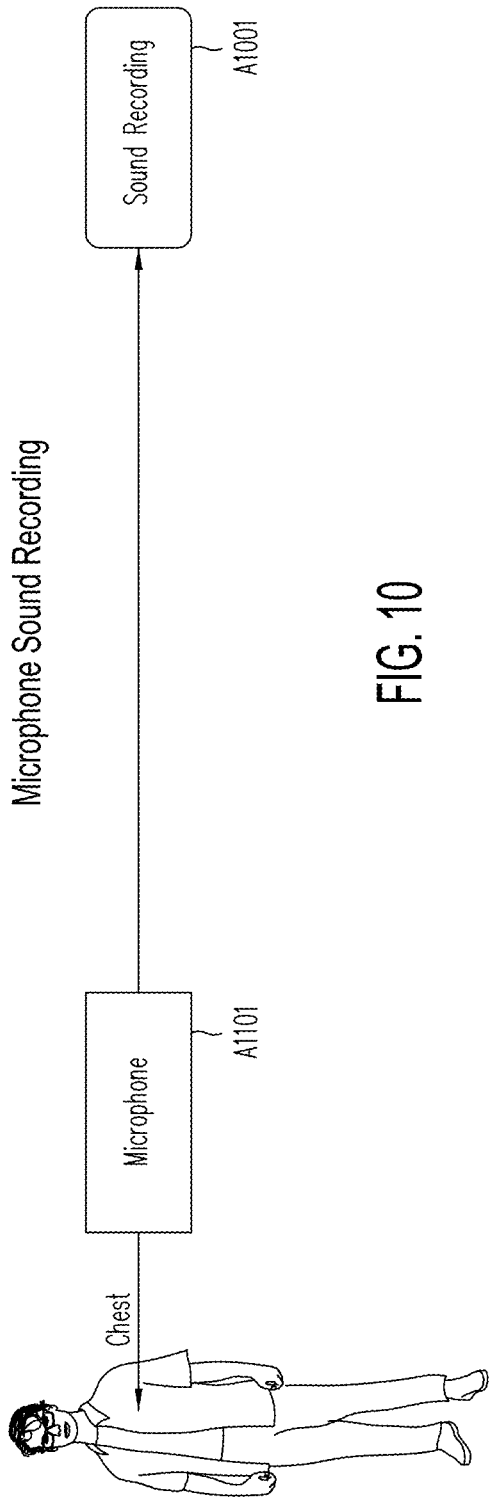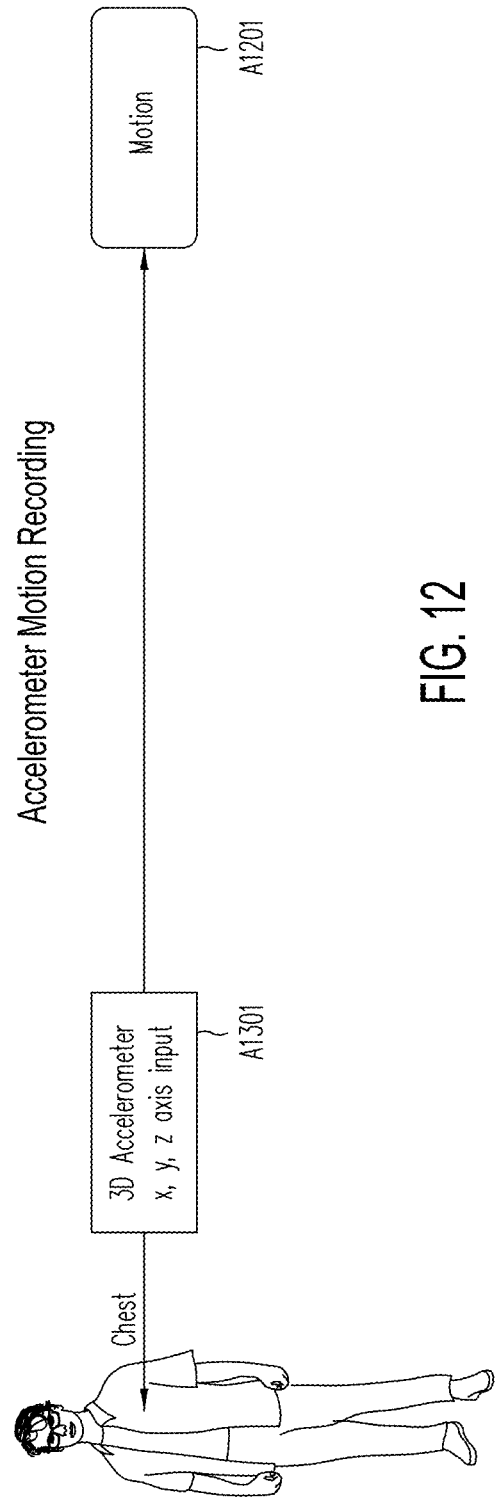

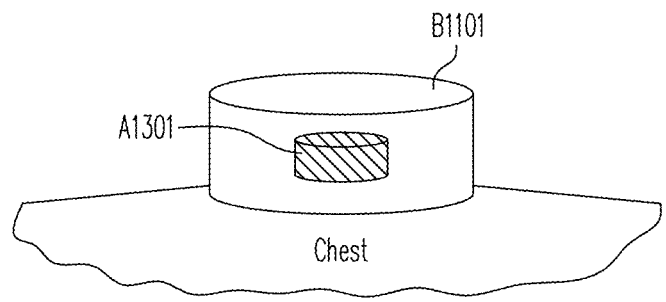
FIG. 13B
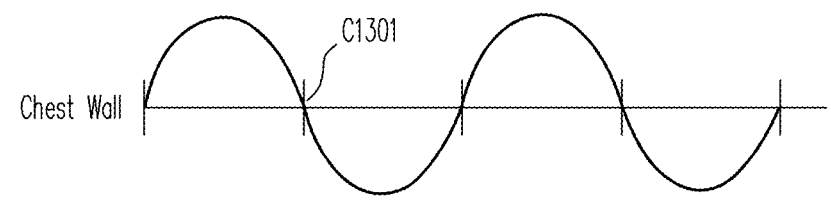
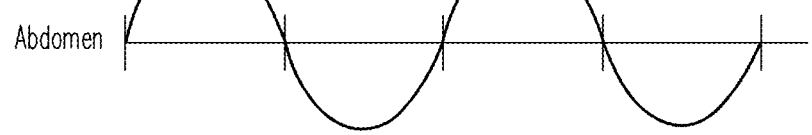
FIG. 13C

KEY TO

PORTABLE DEVICE WITH MULTIPLE INTEGRATED SENSORS FOR VITAL SIGNS SCANNING

CROSS REFERENCE TO RELATED APPLICATIONS

This application is a continuation application claiming the benefit of U.S. Non-Provisional patent application Ser. No. 14/704,961, entitled PORTABLE DEVICE WITH MULTIPLE INTEGRATED SENSORS FOR VITAL SIGNS SCANNING filed on May 5, 2014 by Bernard Burg et al. which is incorporated herein by reference for all purposes. U.S. application Ser. No. 14/704,961 claims the benefit of U.S. Provisional Patent Application Ser. No. 61/988,899, entitled PORTABLE DEVICE WITH MULTIPLE INTEGRATED SENSORS FOR VITAL SIGNS SCANNING filed on May 5, 2014 by Bernard Burg et al. which is incorporated herein by reference for all purposes.

This application is also related to U.S. patent application Ser. No. 14/641,303, filed on Mar. 6, 2015 by Max Little et al. and U.S. patent application Ser. No. 12/292,820, filed on May 30, 2014 by Wenyi Zhao et al., both of which are incorporated herein by reference for all intents and purposes. U.S. patent application Ser. No. 14/641,303 claims the benefit of U.S. Provisional Patent Application Ser. No. 61/949,235, filed on Mar. 6, 2014 by Max Little et al. U.S. patent application Ser. No. 12/292,820 claims the benefit of U.S. Provisional Patent Application Ser. No. 61/924,230, filed on Jan. 6, 2014 by Wenyi Zhao et al.

FIELD OF THE INVENTION

This invention generally relates to vital signs scanning by a portable device with multiple integrated sensors.

BACKGROUND OF THE INVENTION

Healthcare is a key element of any modern society. Self-monitoring and early detection are key elements to prevent and control diseases and pain while keeping costs in check. Modern technology brings medical accuracy devices to end-users allowing them to collect measurements more frequently, with privacy in their home environment, or office. These new devices bring a tremendous change in medicine leading from a few measurement points taken during doctor appointments and clinic visits to a nearly continuous set of measurements that may be automatically downloaded to personal medical records. The quantity of this data linked to their sampling frequency allows new types of data interpretation. For example, trends and tendencies will allow predictions and predictive measures rather than detecting after-the-fact events as currently done in the art.

To be adopted in the market and become a medical success, vital sign measurement devices should be user friendly and simple to use so they can be used daily, such as a shaver, a hair dryer or a microwave oven. Measurements with vital sign measurement devices could become part of a daily routine or used sporadically throughout the day. An ubiquitous vital signs measuring device may include advantageous features. The ubiquitous vital signs measuring device is a single integrated device that makes a plurality of vital sign measurements in a short time period for user friendliness. The vital sign measurements are quick and discrete; instead of taking a few minutes of time to set up and use, being noisy and very explicit about the type of vital sign measurements being performed, such is the case with a blood pressure cuff for example. In this manner, a user can perform the vital sign measurements without embarrassment during their daily routine at home or office. The user interface for the measuring device can show useful user-friendly results to a user. The vital sign results from the measurement device are locally stored and can be sent to remote servers in a transparent manner, such as with electronic/personal health records for example.

Individual Measurements

It is advantageous for vital signs measuring devices to cover a large range of measurements to monitor as many conditions, or signs, as possible. That way, the vital signs measuring devices can be useful to as many users as possible. Some users monitor a set of pathologies with a precise type of measurements prescribed by medical teams, whereas others monitor their bodies out of curiosity, to better know themselves, or to monitor for trends. Some important measurements include: temperature, heart rate, pulse rate, blood oxygenation, blood pressure (systolic and diastolic), and respiration rate.

Additional measurements such as recording sounds and motions can be interpreted in many ways including respiration rate, and more generally lung and heart functions. Also, accelerometers, gyroscopes and GPS have been the foundation of sports and fitness devices as well as activity monitoring.

Many individual vital sign measurement devices have been developed that focus on measuring one type of vital sign of a patient. There are often four vital signs that are desirable to measure for a patient. Typically, four individual separate vital sign measurement devices are used to measure these four vital signs such as a thermometer, a pulse-oximeter, a blood pressure cuff, and an electrocardiogram (ECG) monitor. The user typically performs these measurements sequentially over several steps. Sequentially performing all of these measurements may from five to seven minutes when using four independent devices. The separate vital sign measurement devices are often large in size and thus are not portable.

SUMMARY OF THE INVENTION

The embodiments of the invention are summarized by the claims that follow below. However briefly, the embodiments of the invention concurrently take at least four vital signs measurements in parallel during the same measurement period using one integrated vital signs scanning device.

To perform physiological measurements for vital signs monitoring, a plurality of sensors are integrated into the vital signs scanner, including a temperature sensor (thermometer), an ECG sensor, dual—red and infrared—photoplethysmographic (PPG) sensors, a sound sensor (microphone), and a motion sensor (3D accelerometers) under the control of a centralized signal processor. These sensors allow the concurrent capture of a plurality of vital signs measurements including, core temperature, heart rate, pulse rate, blood oxygenation (SpO2), respiration rate, and blood pressure.

The vital signs scanner of the embodiments of the invention is battery operated and has a compact form factor that allows it to be a portable vital signs scanner. The vital signs scanner may be one hundred times more compact than the individual measurement devices that it can replace. The compact form factor allows it to readily fit within a user's pocket or purse for example.

The vital signs scanner of the embodiments of the invention is automated, user friendly, and convenient to use. The automation in the vital signs scanner of the embodiments of the invention reduces the time to capture vital signs data and improves the usability of a vital signs scanning device. The user of the vital signs scanner of the embodiments of the invention can focus on taking quality measurements at the right times. Automated data processing operations of the vital signs scanner are transparent to the user. There is no need to inflate a cuff. The vital signs scanner of the embodiments of the invention has a quick start up time avoiding wait times to boot up or go through a warm up phase. The vital signs scanner of the embodiments of the invention records and stores results. That way, a user can avoid writing results down on paper with a pen/pencil. The vital signs scanner of the embodiments of the invention uses signal processing techniques to take the vital signs measurements during a measuring session so that inconveniences, such as a blood pressure cuff and a noisy pump to inflate it, are avoided.

A Coherent Set of Measurements

Taking measurements in parallel brings new challenges, new opportunities and therefore requires new solutions. Measurements should be completed within each measurement session. Simultaneous measurements with several sensors may be affected by mutual interference. Interactions between sensors need to be studied, hence creating new challenges.

A plurality of vital sign sensors in a unified scanner can provide concurrent capture of a plurality of vital signs measurements including, core temperature, heart rate, pulse rate, blood oxygenation (SpO2), respiration rate, and blood pressure.

However, all these measurements share a time base as well as some noise since all the measurements are performed by a single vital signs scanning device. Mechanical noise like motion and vibration, lighting conditions, and ambient temperature are common measurements that may be captured with the vital signs scanning device. Capturing a measure of these noise sources allows the vital signs scanner to perform noise cancellation to improve signal to noise ratios and take corrective actions if the signals are too poor to obtain useful measurements.

With a coherent time base for the plurality of different types of sensor data, the sensor fusion may be applied to the signals obtained from individual sensors to enhance the data through redundancy and cross-validation.

BRIEF DESCRIPTION OF THE DRAWINGS

For the purpose of facilitating understanding of the invention, the accompanying drawings and description illustrate preferred embodiments thereof, from which the invention, various embodiments of its structures, construction and method of operation, and many advantages may be understood and appreciated.

FIG. 4B illustrates details of an ECG to patient interaction model.

FIGS. 4C-4E illustrates exemplary heart rate physiological models.

FIG. 10 illustrates an exemplary process of taking sound recordings.

FIG. 12 illustrates an exemplary process of taking accelerometer motion recordings.

FIG. 13B illustrates an exemplary accelerometer to patient interaction model.

FIG. 13C illustrates an exemplary accelerometer physiological model.

DETAILED DESCRIPTION

In the following detailed description of the embodiments of the invention, numerous specific details are set forth in order to provide a thorough understanding of the embodiments of the invention. However, it will be obvious to one skilled in the art that the embodiments of the invention may be practiced without these specific details. In other instances well known methods, procedures, components, and circuits have not been described in detail so as not to unnecessarily obscure aspects of the embodiments of the invention.

The embodiments of the invention include a method, apparatus and system for a portable vital signs scanner with a plurality of integrated sensors.

Holding the Device

Figure 1:
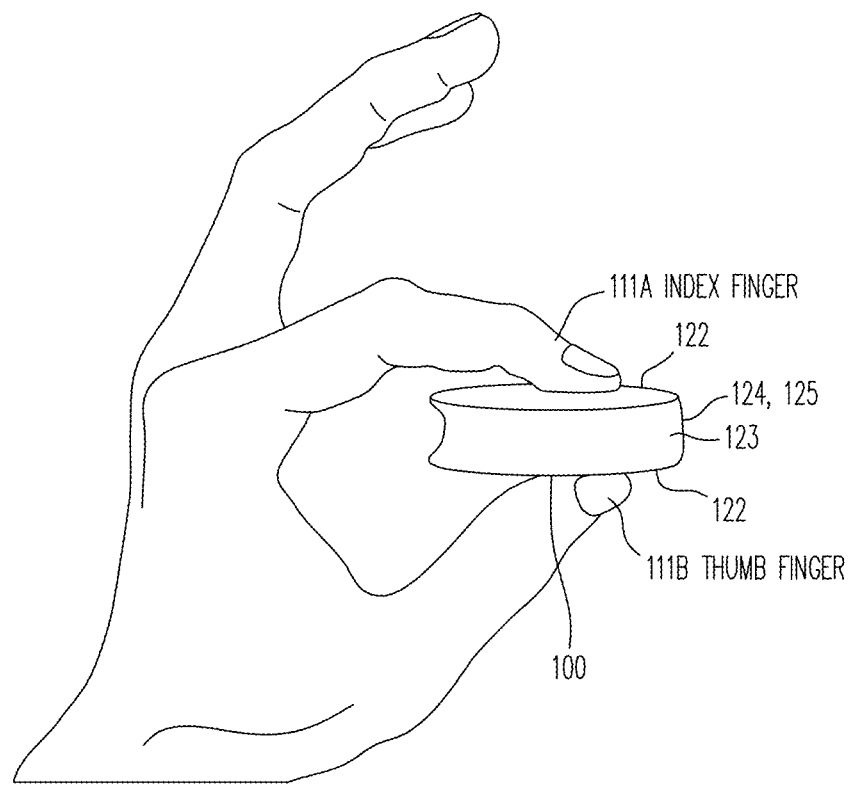
FIG. 1 illustrates a user holding the device between index finger and thumb.

Referring now to FIG. 1, an exemplary use of a vital signs scanner 100 is shown. In FIG. 1, the user holds the vital signs scanning device 100 between the index 111A and thumb 111B of a left hand making contact with an ECG electrode 122 under the index finger, the thumb, or both. The user pushes the vital signs scanner 100 lightly against the left temple or forehead for a period of time. Doing so, an ECG electrode 123 of the side of the vital signs scanner 100 makes contact with the left temple or forehead of the user. A thermometer sensor 125 and a PPG sensor 124 near the electrode 123 are also applied over the temple or forehead of the user. One or more accelerometers within the vital signs scanner 100 are attached to a printed circuit board (PCB), which is linked to the housing of the scanning device 100 casing. The vital signs scanner 100 also includes a microphone. Accordingly, the vital signs scanner 100 can concurrently capture sounds with the microphone and movement with the accelerometer as vital sign signals are being captured by other sensors.

Note that positions of fingers/thumb are shown in the figures for explanatory purposes. However, positioning of fingers on the vital signs scanner 100 can vary depending on the implementation. For example, in another implementation, the index finger 111A and the thumb finger 111B may be positioned on the sides of the scanner with one or both coupling to an ECG electrode to complete the circuit through the body with the second ECG electrode 123.

Figure 13A:
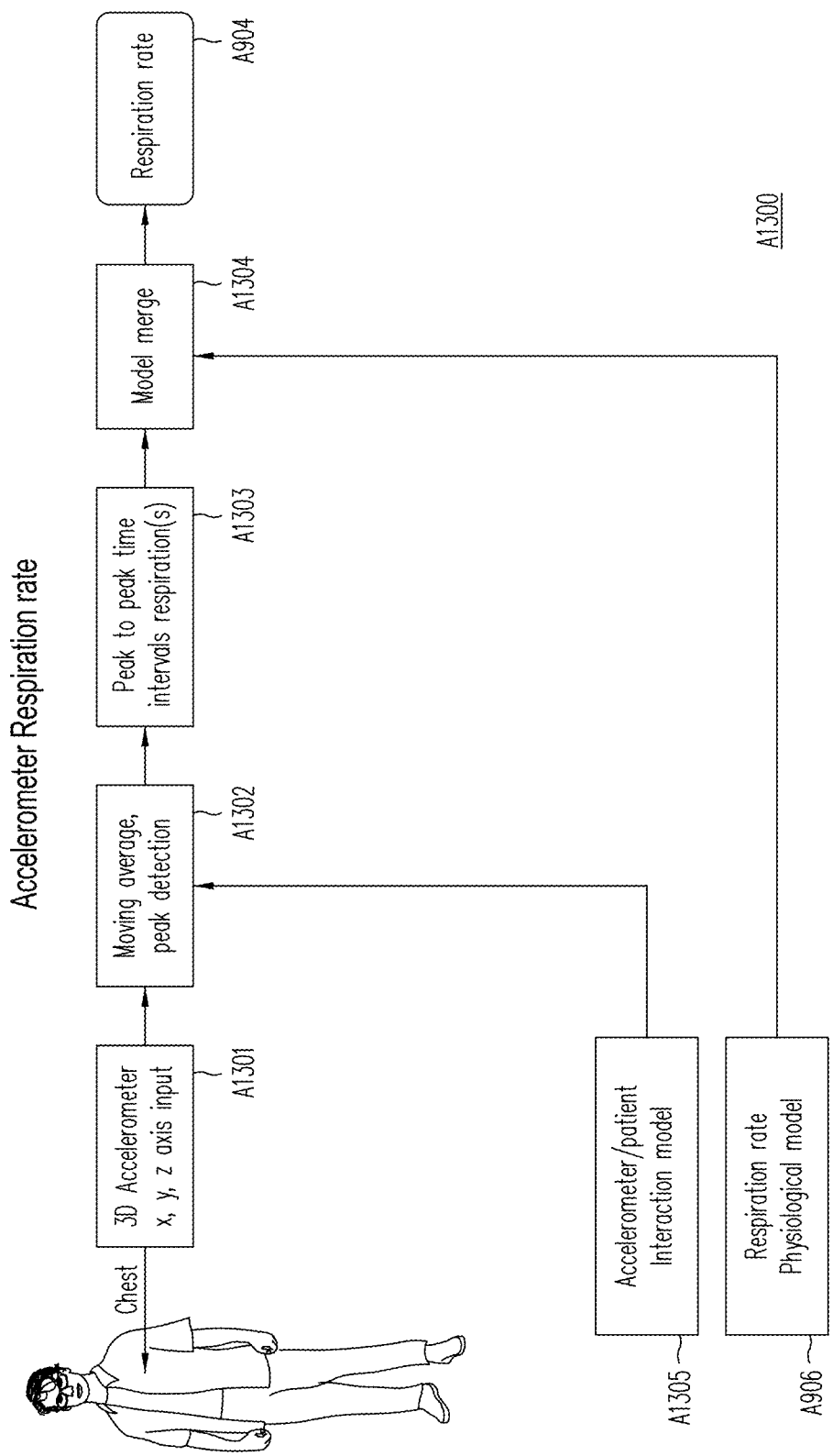
FIG. 13A is a flow chart illustrating an exemplary accelerometer based process of measuring respiration rate.

In another example of use, such as shown in FIGS. 13A-13B, the vital signs scanning device 100 is pushed flat against the chest to capture sounds with a microphone and motion of the chest with one or more accelerometers over another period of time.

Location of Sensors

Figure 2B:
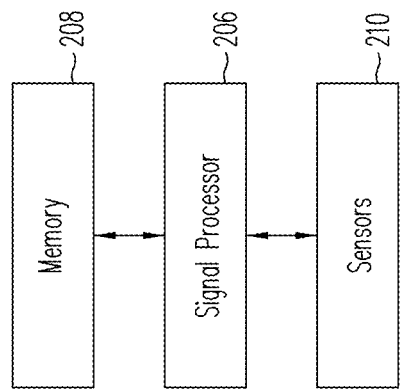
FIG. 2B illustrates a functional block diagram of the signal processor used within the vital signs scanner 100.
Figure 2A:
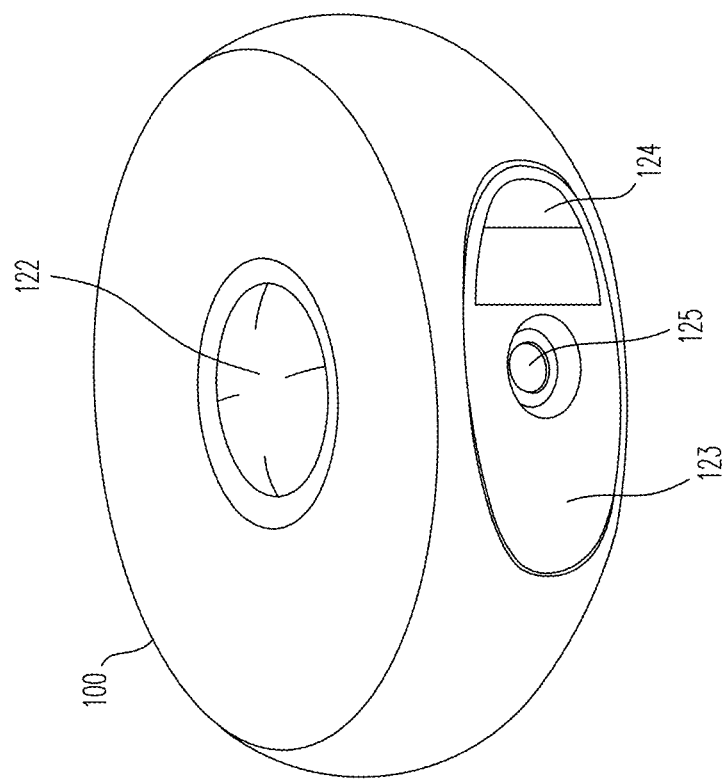
FIG. 2A illustrates a perspective view of an exemplary embodiment of the invention.

FIG. 2A illustrates exemplary locations of the sensors in accordance with one embodiment of the invention. The ECG electrode 122 may be positioned under the index finger 111A, the thumb 111B, or both finger and thumb and squeezed by the user. The ECG electrode 123 is positioned against the temple/forehead of the user. With the ECG electrodes making contact, the ECG sensor closes an electric circuit with the users body including a circuit path through hand, arm, and heart to the temple.

Studies; such as Comparison of temporal artery to mercury and digital measurement in pediatrics by Isler, A., et al., published in 2013 by the *International Emergency Nursing*, (see http://dx.doi.org/10.1016/j.ienj.2013.09.003); have shown that the temporal artery near the temple is a privileged place to sense temperature with high accuracy. Accordingly, the thermometer sensor 125 can directly sense the surface temperature at the temple or forehead of the user.

PPG sensors 124 shown in FIG. 2A are also for sensing at the user's temple. The primary advantage of the temple location over, for example, a wrist location is that the construction of the vascular tunics in terms of presence/content of tissue elasticity greatly influences "signal fidelity". For example, readings at the temple are much more representative than readings at the wrist, which includes an entirely greater percentage of elastic tissue in the arterial tunics, etc.

The temple may also be a good location to take PPG measurements because it is in direct connection to the heart via the temporal artery. Unlike the fingers/thumb being used for PPG measurements of known pulse-oximeters, the blood flow at the temple is only marginally modified by body configurations (straight head, turned head, standing, sitting). With such freedom in body configurations, the temple PPG measurements put fewer constraints on a user in an uncontrolled environment. The scanning device 100 senses for vital sign parameters with sensors at some of the most reliable sites on the body while minimizing inconvenience to users.

Figure 18:
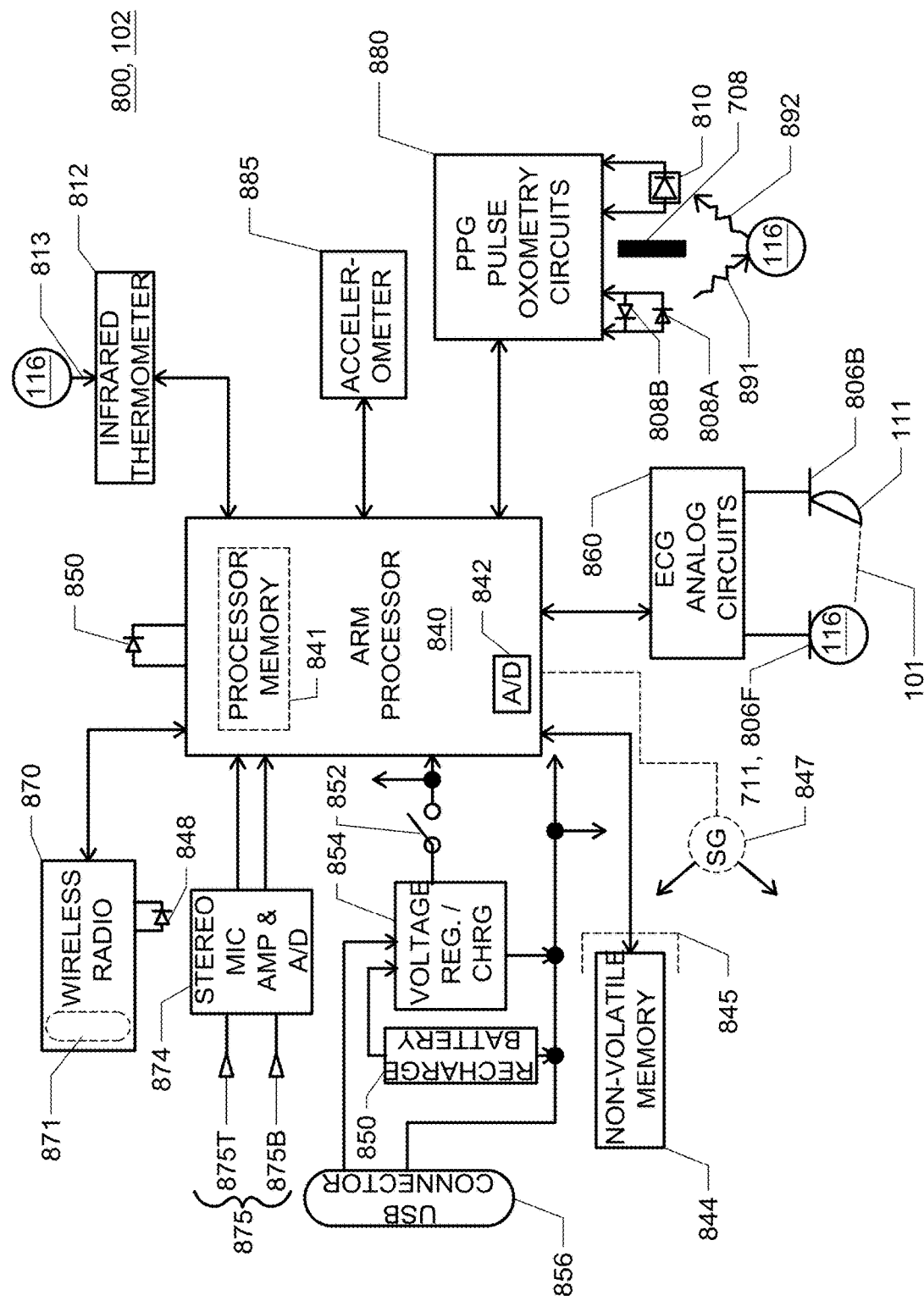
FIG. 18 illustrates a functional block diagram of electronic circuitry within the exemplary portable wireless vital signs scanner.

Referring now to FIG. 2B, the vital signs scanner 100 includes a signal processor 206 with a storage device 208 and a plurality of sensors 210 coupled to the signal processor 206. The signal processor 206 controls the plurality of sensors 210 to concurrently capture data during the measurement period. The processor 206 is coupled to a storage device 208, such as memory, to read instructions and execute signal processing algorithms to achieve the methods of generating vital sign measurements as described herein. A number of algorithmic models may be further stored within the memory that are used by the signal processing algorithms executed by the processor 206. For each type of measurement performed by the vital signs scanning device 100, enhanced measurement models are used that link three types of partial models together. A schematic diagram of the vital signs scanner 100 is shown in FIG. 18 and described herein.

A first partial model is a signal processing model that is performed on the signal generated by a sensor. The analog signal generated by the sensor is transformed by an analog to digital conversion into a digital signal. The digital signal then undergoes an initial signal processing by a signal processor with a signal processing algorithm to typically remove noise. Noise in many optoelectronic devices, such as the PPG photodiodes, is removed before it gets to the signal processor and the signal processing algorithms. For example, after the photon current from the detector is converted to voltage through a transimpedance amplifer (e.g., Z Amp), the Z Amp noise can be removed with a "chop circuit" that chops out the noise and any float in the op amp offset voltage float. The signal processing algorithm may then further perform additional transformations or data processing before finally providing the resulting vital signs measurement value to be displayed to users or stored in healthcare records.

The second partial model is an interaction model that captures the interaction between the user and the sensor. This interaction model may entail hysteresis or inertia for some sensors, such as a temperature sensor. For other sensors, the interaction model may include the noise affects that a user may introduce, such as light pollution noise for PPG sensors or vibration noise for accelerometers sensing motion. The interaction model may include models of the contact between sensor and the user's body. For example, physical properties of the skin like conductivity, elasticity or color may be something to consider when a sensor makes contact with the user's body. Including the interaction model as an explicit part of methods of obtaining vital signs from a user with the vital signs scanner 100, signal processing algorithms may embed the interaction model, leverage and correct them to provide improved vital signs measurement results. Furthermore, a sensor may be used in a plurality of body sites to obtain different vital signs. The interaction model may have different interactive conditions with the vital signs scanner for the different positions of the scanner with the same sensor. Accordingly, embodiments of the invention may change to a different interaction model in response to the vital sign being captured and the use of the sensor at different body locations.

A third partial model is a physiological model. The physiological model is linked to the measured vital sign. Human physiology has been studied for centuries, worldwide. Early medical studies by Ambroise Paré (1510-1590) led from belief to evidence and eventually to the science of medicine, modeling vital functions and generating vital signs as a measure of that function.

Medical or physiological models are often the building blocks of medical terminology. For example, medical students learn to analyze ECG patterns based on the P, Q, R, S, T phases of an ECG signal model for a human. Another commonly known physiological range for heart rate of a human is that heart beat rates vary between 25 beats per minute and 250 beats per minute. Another commonly known physiological model for temperature is that core temperatures of a human vary between 28 degrees centigrade (C) and 43 degrees centigrade.

In the vital signs scanner 100, physiological models may be used by the signal processor and its signal processing algorithms to validate the resulting vital sign measurements. A mathematically correct signal generated by a sensor and sent to the signal processor for signal processing may be deemed noise for physiological reasons. For example, a sampling of the body temperature at a frequency of 10 Hertz (Hz) may show some variation in the temperature signal up to 5 Hz according to Nyquist-Shannon sampling theorem. However, the physiological models of temperature exclude any temperature variation above 0.015 K/s. This is because a human body under normal conditions, is unable to change temperature faster. Accordingly, variations in the temperature signal at higher rates are likely to be noise that can be eliminated.

The signal processing provided by the vital signs scanner combines these three models together in the process of generating vital signs values. The vital signs scanner and signal processor therein uses signal processing methods to extract the signal mathematically relevant within the sampling rate of the device, according to the Nyquist-Shannon sampling theorem. The vital signs scanner and signal processor therein uses a sensor interaction model to perform corrections linked to pollutions of readings such as noise generated at the interaction point due to both the human side of the measurement point and the physical characteristics of the sensor. The vital signs scanner and signal processor therein further uses the physiological model of the measurement where the human body parameters remain in a family of possible ranges, shapes, dynamic and bandwidth of signal.

A valid measurement for a vital sign should comply with these partial models. A valid measurement for a vital sign should be mathematically correct regarding signal processing. The contact interaction for a valid measurement for a vital sign should be validated and corrected during the duration or length of time of the measurement. The measured signal for a valid vital sign measurement should be medically relevant.

The methods and signal processing algorithms used by the vital signs scanner and its signal processor can introduce corrections at each step, for each partial model, resulting in a high accuracy measurement, for each measurement (temperature, heart rate, pulse rate, blood oxygenation, blood pressure, respiration rate), each of which is performed at some of the best sites on the body (temple, forehead, finger/thumb).

The methods and signal processing algorithms used by the vital signs scanner and its signal processor may also use a sensor fusion model to leverage multiple measurements and improve the results of one or more different types of measurements through data fusion. The vital signs scanner 100 concurrently captures signals from its sensors during the same measurement periods. Accordingly, the signal data for one or more of a plurality of sensors may be used to improve the signal data and measurement results for another sensor and vital sign. Some signal pollution (e.g., signal noises) are shared across a plurality of sensors due to their physical location and their shared mechanical link in the housing or device enclosure of the vital signs scanner 100. For example, an accelerometer measures the motion and vibrations of the vital signs scanning device, deleting motion artifacts. The motion and vibrations of the vital sign scanner can be coupled to the signal processor or fed back to other sensors during signal interpretation, to either validate or invalidate the data, or to make data corrections to improve the signal data.

Thermometer and Temperature Measurement

Figure 3A:
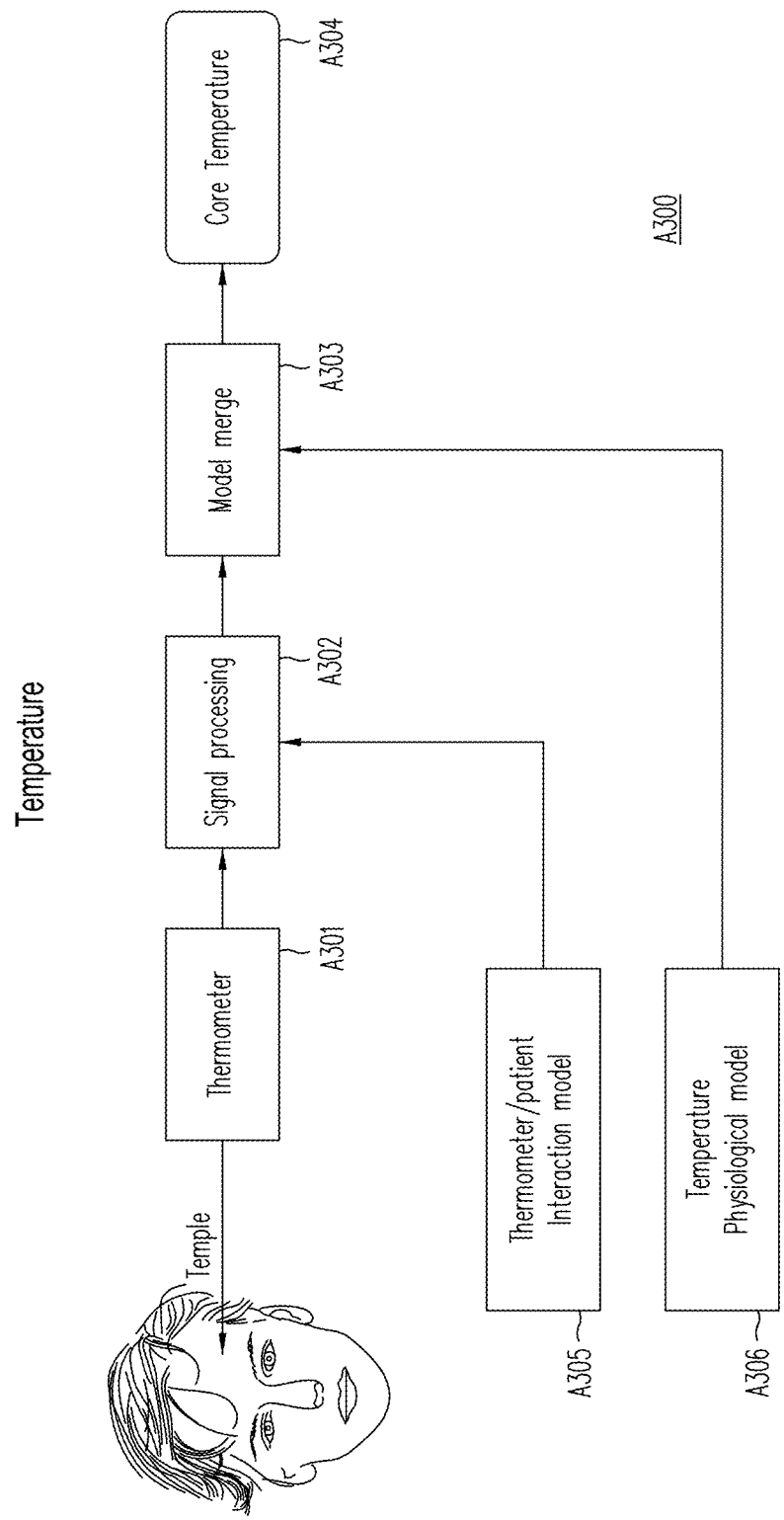
FIG. 3A provides a flow chart description of an exemplary process of measuring temperature.

Referring to the flow chart shown in FIG. 3A, a temperature sensor or thermometer device A301 is pressed against the temple of the user to measure the surface temperature above the temporal artery. The output signals from the thermometer is coupled into a signal processing module A302 to signal processing.

The signal processing module A302, such as by an FFT/IFFT for example, initially removes noise in the output signals from the thermometer sensors to obtain what is expected to be a desired data signal. The data signal is further processed by the signal processing module A302 taking into account the thermometer-patient interaction model A305. A validation signal is generated by the signal processing module A302 when the sensor readings are stable (see FIGS. 3B and 3C and description thereof) or have sufficiently low noise, and are within expected ranges. With a valid data signal, further processing can occur.

The resulting valid data signal is coupled into a model merge module A303. The model merge module A303 calculates the value of the core temperature $T_c$ according to formula $$T_c = k(T_s - T_a) + T_a$$

where $T_a$ is the ambient temperature, $T_s$ is the skin temperature, both of which are measured in parallel by two different thermometer elements. The value of k for the core temperature equation is an experimental calibration parameter obtained by quadratic approximation, such as described for example in the "Temperature Assessment via the Temporal Artery: Validation of a New Method", by Marybeth Pompei, published by Exergen Corporation, copyright 1999. The core temperature $T_c$ is then checked for physiological validity against the temperature physiological model A306 (see additional explanation with reference to FIG. 3D). The overall temperature result A304 is displayed to a user and/or stored into health records.

Figure 3B:
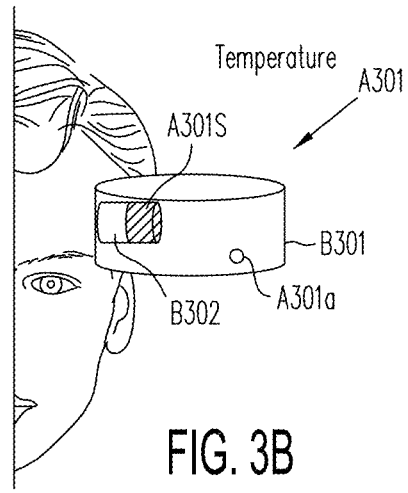
FIG. 3B illustrates a thermometer to patient interaction model.

An example of positioning of the thermometer device A301 is shown in FIG. 3B. The thermometer device A301 is applied against the temple of the user. The thermometer device A301 includes an ambient temperature sensor A301a and a surface temperature sensor A301s, both of which concurrently take measurements in parallel together with the other vital signs.

By construction, the surface temperature sensor A301s is receded in the housing B301 of the vital signs scanner. The surface temperature sensor A301s does not make direct contact with the skin of the user, instead taking its measurement through a copula of air B302. This copula of air B302 offers a small thermic inertia that is taken into account by the thermometer-patient interaction model. Using the air copula B302 to avoid the sensor from directly touching skin, complex interaction models can be avoided. Furthermore, the sensor avoids being soiled by skin products, sweat etc. that may be on a user's skin.

Figure 3C:
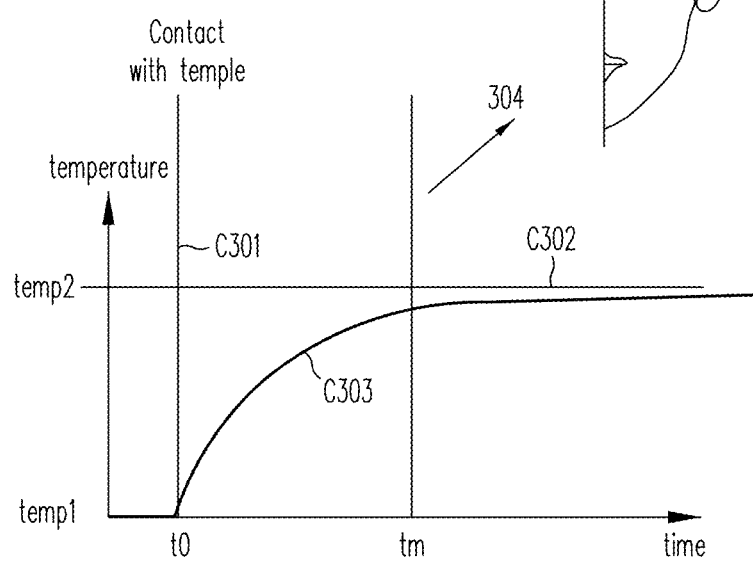
FIGS. 3C-3D illustrates an exemplary temperature physiological model.

FIG. 3C illustrates an exemplary thermometer-patient interaction model showing the thermometer output signal C303 varying over time. Prior to contacting the user temple at time t0 at C301, the output signal C303 is constant at temp1. After time t0, the thermometer signal C303 grows to reach an asymptote C302 of temp2. The thermometer-patient model provides a threshold time tm C304 after contact that needs to be exceeded before validating the asymptote C302 to be output temporal temperature once the signal has stabilized. One mechanism of such an algorithm measures the relative variation of the signal over time. Thus, this algorithm can also function when the thermometer is removed from the temple of the user.

Figure 3D:
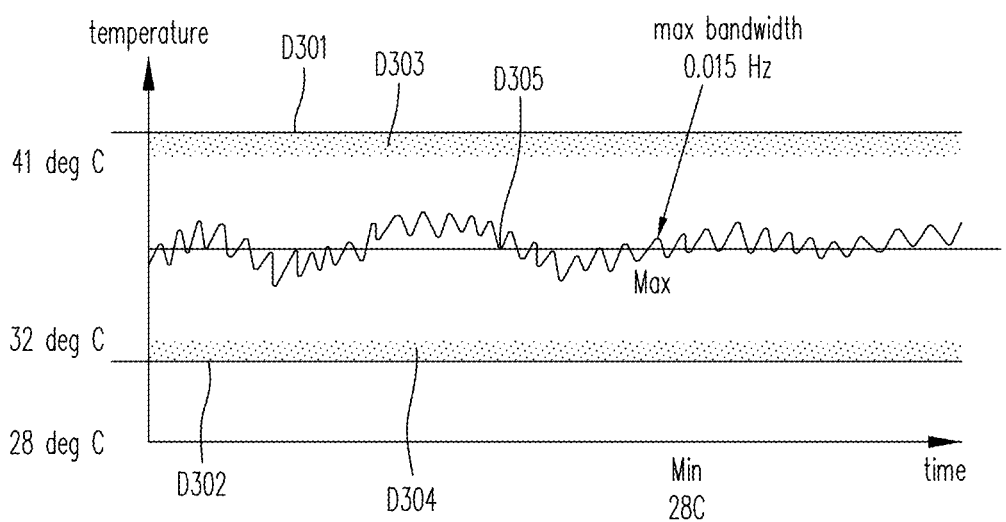

FIG. 3D illustrates an exemplary temperature physiological model for determining core temperature. The chart of the model illustrates lines D301,D302,D303,D304 representing ranges within which the temperature signal for the user is not going to exceed. Signal D305 represents a raw temperature signal from the thermometer.

Living humans can function between twenty-eight degrees centigrade (28° C.) (e.g., see line D302) and forty three degrees centigrade (43° C.) (e.g., see line D301). The temperature physiological model illustrates that medical emergencies are declared for temperatures below 32° C. (e.g., see line D304) and temperatures above 41° C. (e.g., see line D303) during a scan. Otherwise, the vital signs scanner can assume that the user is not undergoing a medical emergency when it is not being used.

In addition, core temperature of the body varies only slowly in time due to thermodynamic principles and the volume of blood in the body. As such, the temperature physiological model has a bandwidth limited to 0.015 K/s or 0.015 Hertz (Hz). With respect to the signal D305, this means that temperature variations at higher rates should be discarded. This is because signal components changing at higher rates of frequency are physiologically impossible. Accordingly, a low pass filter with cutoff near the bandwidth limitation of 0.015 Hz can be used to filter out the signal components changing at the higher rates of frequency from the temperature signal as noise.

ECG and Heart Rate

The calculation of ECG and heart rate vital sign values include a noise model and a heart rate physiology model. The noise model provides that peaks lower than a rejection threshold R are to discarded. The noise model further provides that peaks that have a duration less than 0.02 seconds are to be discarded. The heart rate physiology model includes a valid range of heart rates (e.g., 35 beats per minute to 250 beat per minute). Values outside this range are invalid. It further includes an expected signal frequency range with an heart rate variations being limited to a maximum threshold. Signals outside the expected signal frequency range or having larger variation than the maximum threshold are deemed invalid.

Figure 4A:
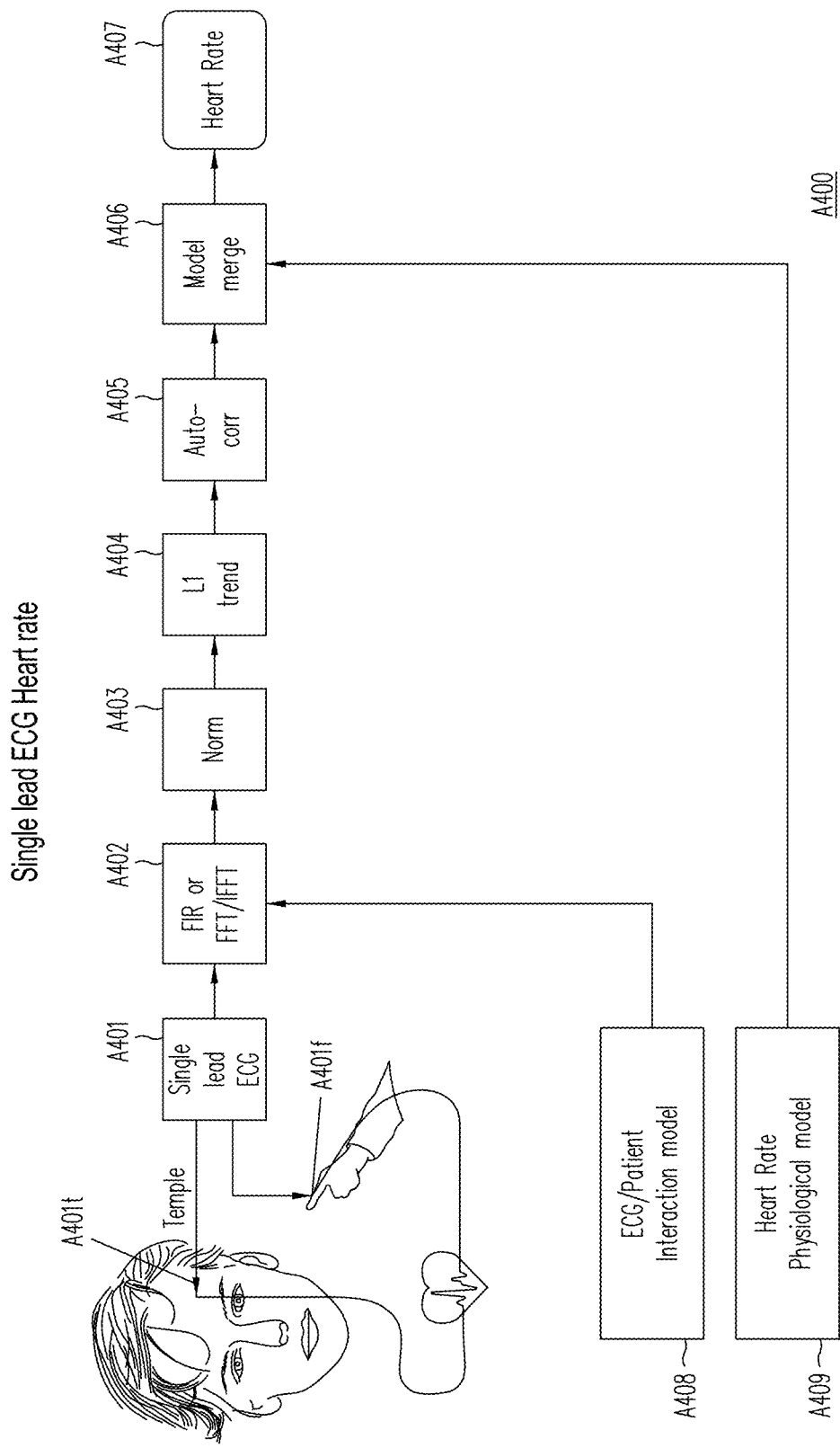
FIG. 4A is a flow chart of an exemplary process of measuring a user's ECG.

Referring to the flow chart shown in FIG. 4A, the ECG sensor A401 closes the electrical circuit between the finger/thumb of the user coupled to the electrode A401f and the temple of the user coupled to the electrode A401t. The output signal from the ECG sensor feeds into a finite impulse response (FIR) or fast Fourier transform/inverse fast Fourier transform (FFT/IFFT) filter A402 removing noise from the data. An ECG-patient interaction model A408 (see also description with reference to FIG. 4B) is used to validate the measurements at this stage. The intensity of filtered ECG signal is then normalized to a normalized signal A403 that is coupled into an L1 trend filter A404. The L1 trend filter A404 produces trend estimates that are piecewise linear, and therefore is well-suited to analyzing time series with an underlying piecewise linear trend. To remove noise, an auto-correlation process A405 by an auto-correlator is performed on the L1 trend filtered ECG signal. The output signal from the auto-correlation A405 is coupled into the model merge process A406. The model merge process A406 merges the ECG physiological model A409 (see additional explanation in FIG. 4C) with the signal processing model. The ECG physiological model A409 is applied to the reduced noise L1 trend filtered ECG signal in order to generate the final heart rate values A407. The heart rate values A407 are shown to the user in a user interface on a display device and/or stored into health records.

An example of positioning of the ECG electrodes is shown in FIG. 4B. When holding the device housing B401, the user's index finger/thumb presses on electrode A401f. With such a grip configuration, the contact between the finger/thumb and the electrode provides a reliable electrical contact. Concurrently, the housing of device B401 is applied against the temple of the user, pushing electrode A401t against the temple or forehead. Due to limited hand stability, small motions made during the measurements. Accordingly, the temple electrode A401t may intermittently lose contact with the temple and generate electrical pollution or noise.

FIG. 4C illustrates an example of ECG signal collected by electrodes B401f and B401t. The ECG signal can be decomposed into intervals (e.g., P, Q, R, S T intervals, which are not shown), with C401 pointing to a QRS complex. However, due to the intermittent contact that may occur as described herein, some additional peaks C402 appear due to the above-mentioned pollution/noise introduced by the sensor-user interaction model. At a first glance, those spikes may be mistaken for the QRS complex C401, but experience showed that the spikes generated by these pollutions, are limited in time to approximately 0.02 seconds.

In contrast, the physiological model produces peaks C401 ranging between 0.12 and 0.20 seconds. Hence the sensor-user model introduces a discrimination between the QRS complex C401 and these intermittent contact spikes C402. One common way to extract the heart rate from the ECG is to extract the R-R intervals D401 of the ECG, as shown in FIG. 4D.

FIG. 4E illustrates an exemplary physiological model for determining heart rates. Each of the heartbeats is represented by a spike E401. The physiological model of the heart rate provides minimum and maximum heartbeats per minute (e.g., 25 to 250 heartbeats per minute for an adult). Another important physiological limitation comes from the heart rate variability, knowing that heart rates cannot vary faster than a given MAXHEARTBEATVARIATION threshold.

PPG and Pulse Rate

PPG and pulse rate calculations use a noise model and a pulse rate physiology model. The noise model is for signals greater than 100 Hertz, for example. The pulse rate physiology model defines a valid pulse rate range between upper and lower values. The pulse rate signals are expected to be within a range of 0.5 Hz to 40 Hz. Pulse rate variations are expected to less than a maximum threshold.

Figure 5A:
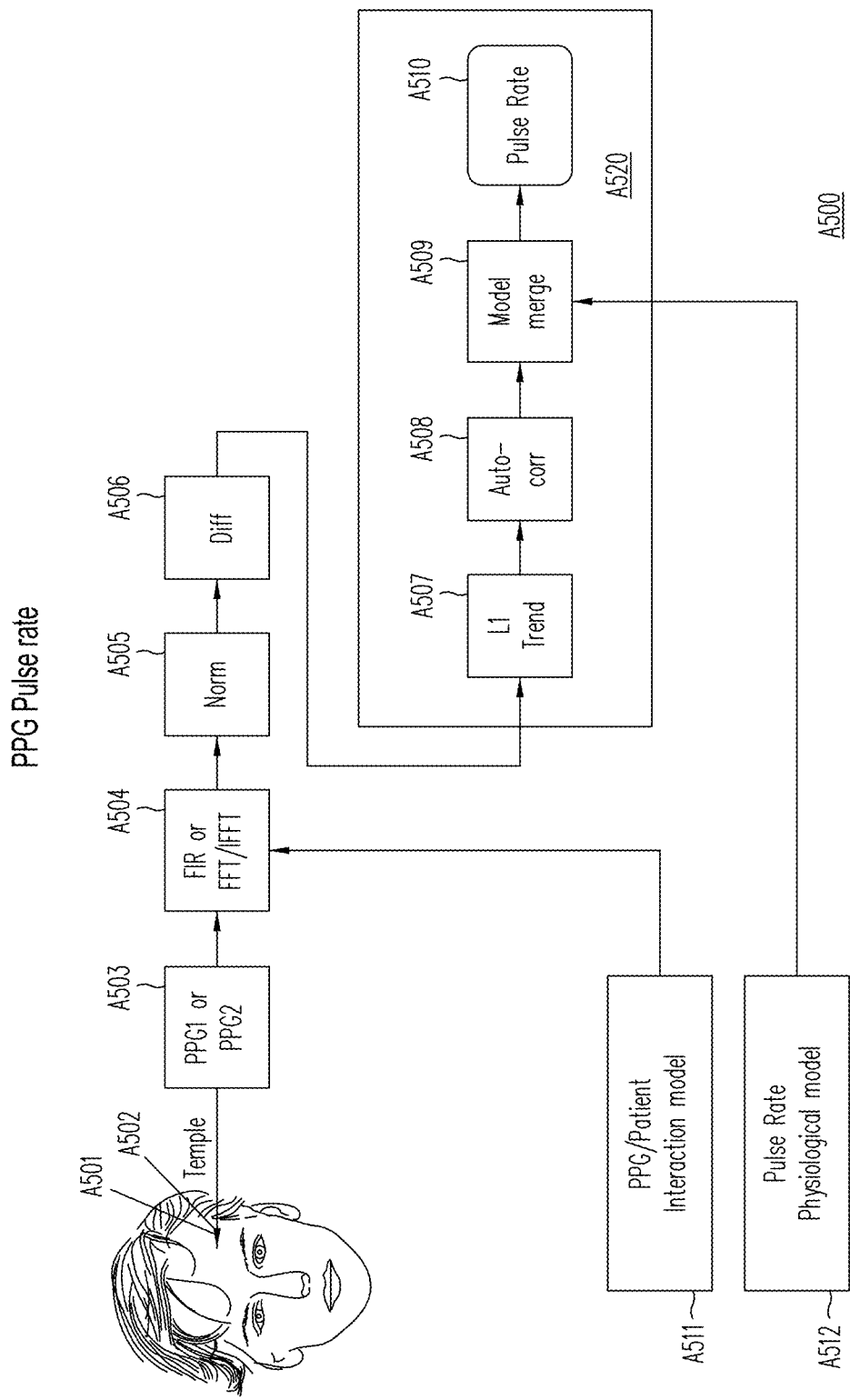
FIG. 5A is a flow chart of an exemplary process of measuring the user's pulse rate.

Referring now to the flow chart shown in FIG. 5A, a pair of photodiode sensors, PPG1 (A501) and PPG2 (A502), are positioned against the temple of the user to capture a PPG signal. One of the photodiode sensors is an infrared (IR) photodiode while the other photodiode sensor is a red photodiode. Only of the signals from the pair of photodiode sensors needs to be used to determine the pulse rate of the user. A selection process A503 selects one of the two raw sensor signals from the photo diode sensors to be processed. While only one signal is shown being processed in FIG. 5A, it is understood that both raw sensor signals may be processed in parallel together for redundancy, noise elimination, and selection of the more reliable pulse rate signal and PPG signal.

The selected raw sensor signal feeds into a FIR or FFT/IFFT filter A504 removing noise from the data. The PPG-patient interaction model A511 of FIG. 5A (see also FIGS. 5B and 5C) is used to validate the measurements in advance at this stage as well. If the signal measurements are invalid, the other photodiode sensor data may be used. If both signal measurements are invalid, the user may be asked to repeat a signal capture process. If valid measurement data is found the signal data, the intensity of this signal is then normalized by a normalization process A505. After signal normalization, the signal is coupled into a first derivative (gradient) filter A506. The output signal from the first derivative (gradient) filter A506 is coupled into an L1 trend filter A507. The filtered data is then coupled into an auto-correlator A508 to undergo an auto-correlation process A508 to remove noise from the filter signal data. The reduced noise signal is then coupled into a merged model A509 that applies the PPG physiological model A512 (see FIG. 5D) to the signal processed signal. The merged model A509 is a math algorithm representative of the PPG physiological model A512. The resulting output from the merged model A509 are pulse rate values A510 of the user. The pulse rate values A510 are displayed to the user by a display device and/or stored into health records.

Figure 5B:
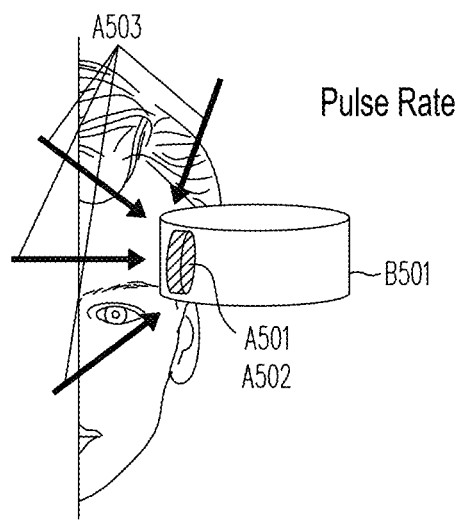
FIG. 5B illustrates an exemplary PPG to patient interaction model.
Figure 6A:
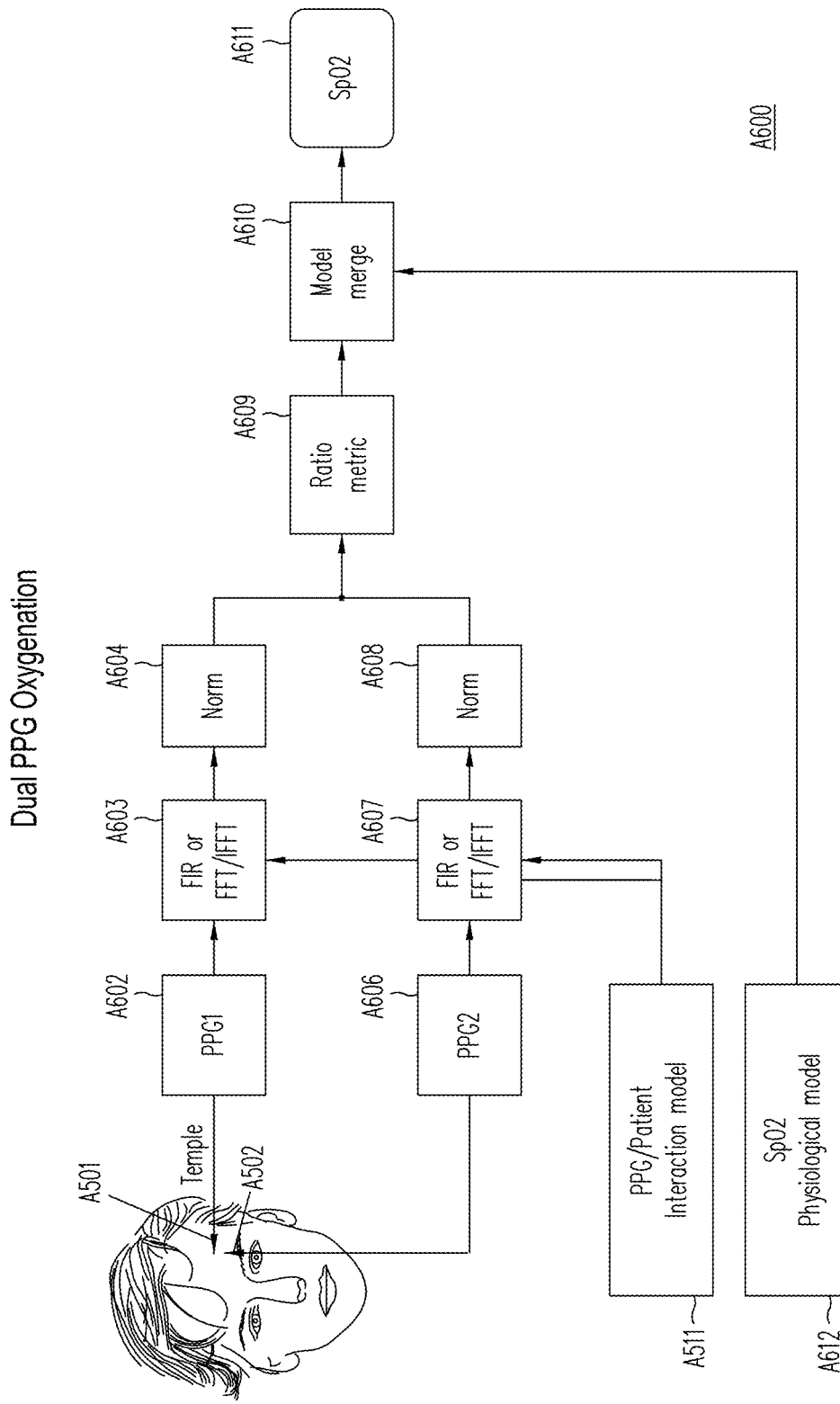
FIG. 6A is a flow chart illustrating an exemplary process of measuring blood oxygenation (SpO2).
Figure 6B:
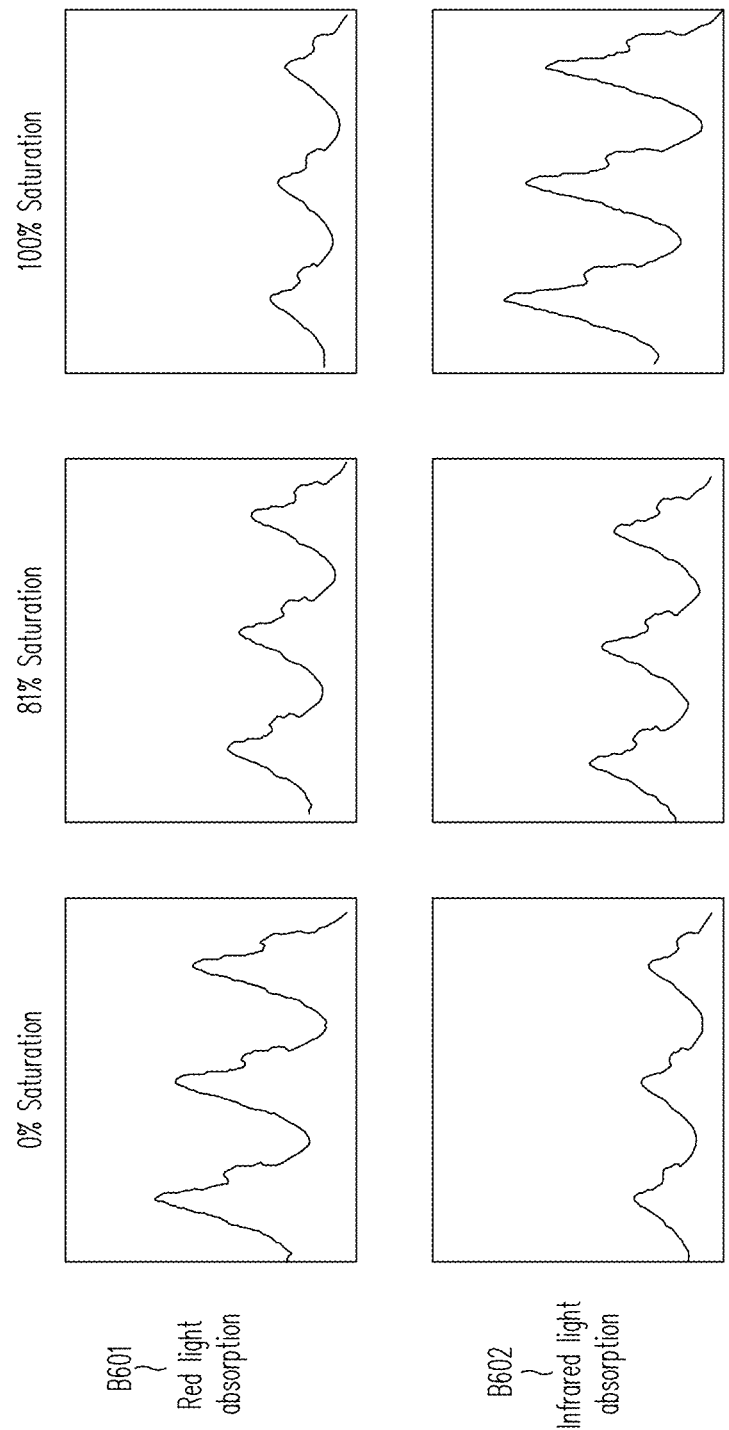
FIGS. 6B-6D illustrate exemplary blood oxygenation physiological models.
Figure 6C:
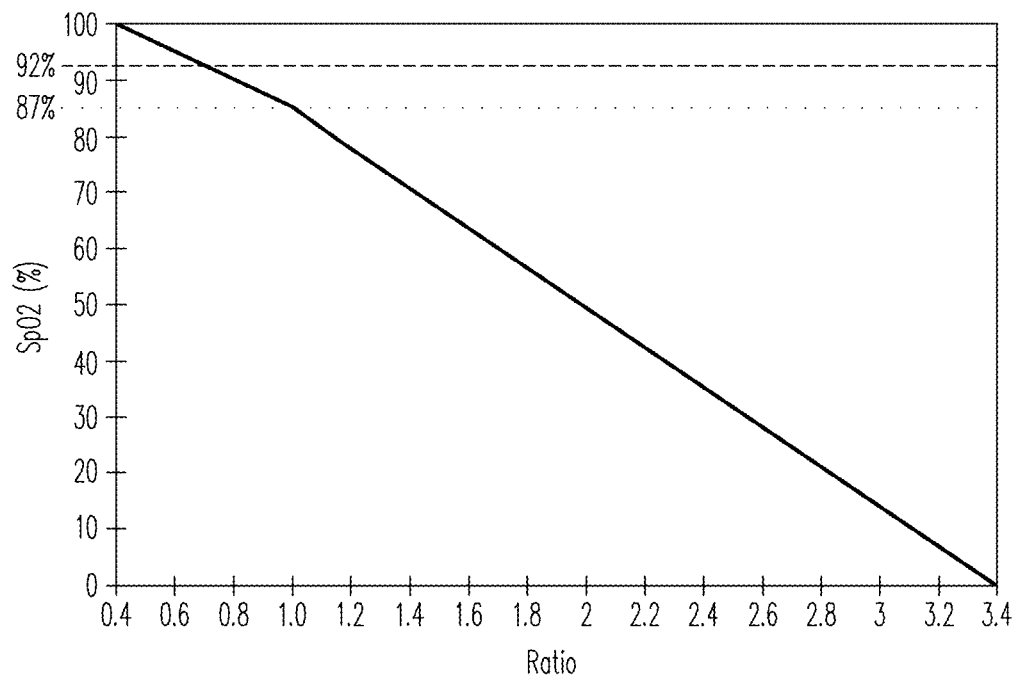
Figure 6D:
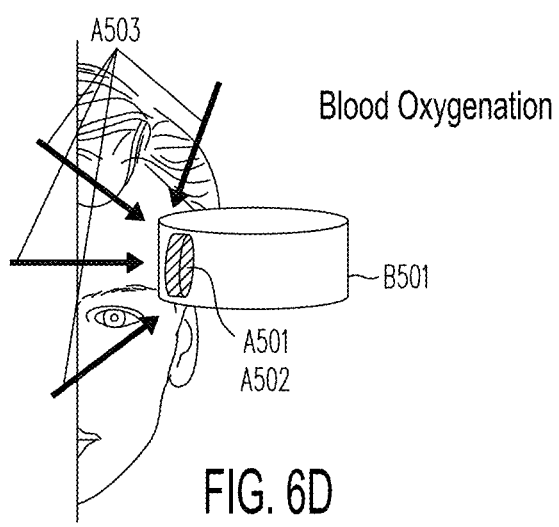

FIGS. 5B and 6D illustrate optimal positioning of the photodiode sensors, PPG1 (A501) and PPG2 A502. When holding the device housing B501 against the temple, the PPG photodiode sensors A501 and A502 are in direct contact with the temple. It is desirable that ambient interfering light A503 from external light sources is blocked by the direct contact. Due to hand instability and other small motions during the measurements, the detector for PPG photodiodes A501 and A502 may intermittently be perturbed by the interfering light A503. This translates into a saturation of the signal.

Figure 5C:
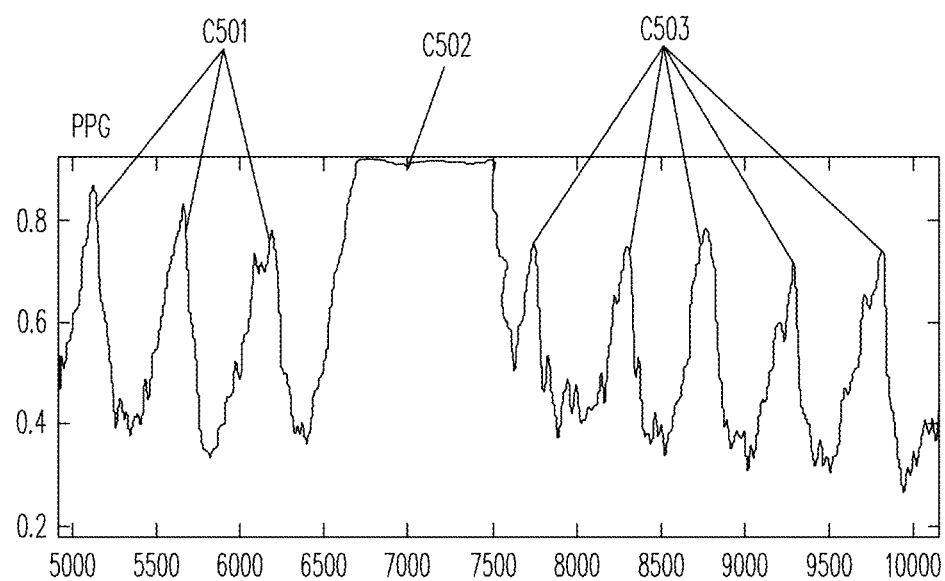
FIGS. 5C-5D illustrates exemplary pulse rate physiological models.

FIG. 5C illustrates a chart of a PPG signal captured with the PPG photodiode sensors A501 and A502 over a period of time. The photodiode sensors capture a signal with a peak C501 and a peak C503 corresponding to each pulse rate. Ambient light perterbation is minimized by the light sheltering design of the housing B501. However, if the PPG was perturbed by interfering light A503, such as due to user hand movement, saturation of the PPG signal may occur as shown at C502. The PPG-user interaction model accounts for ambient light perterbation by using an algorithm to detect and filter out the interfering light.

One example of this algorithm estimates on the fly the frequency (1/Δt) of the pulse rate based on identified peaks C501 and forecasts future peaks (spaced by Δt). When encountering noise pollution like that seen at C502, the peak detection is lost, and the predicted peak positions do not match the signal. The algorithm discards these missed peaks and uses the existing prediction to find peaks at a later time. Once peaks C503 are detected, the algorithm checks that these peaks are compatible with the frequency of the C501 peaks (e.g., $t_{C503\ peaks} = x^* \Delta t + t_{C501\ peaks}$) to finally predict the pulse rate based on all the detected peaks.

Figure 5D:
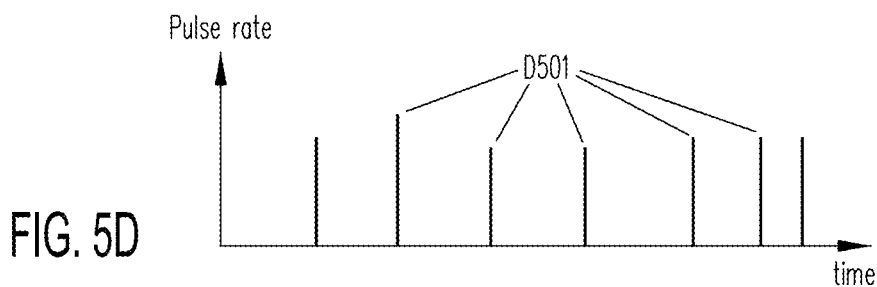

FIG. 5D illustrates an exemplary physiological model for measuring pulse rates. Each of the pulse beats is represented by a spike D501 corresponding to one of the C501 and C503 peaks. The physiological model of the pulse rate provides minimum and maximum pulse beats per minute, typically thirty-five (35) to two hundred fifty (250) beats per minute for an adult. Another important physiological limitation comes from the pulse rate variability. Heart rates cannot vary faster than a maximum heartbeat variation threshold. The maximum heartbeat variation threshold may be incorporated into the physiological model to exclude pulse rate variations that exceed this threshold. Physiological models may also include degenerated pulse signals due to heart conditions, where the pulse may diminish or even vanish when the heart rate increases. Such phenomena may be measured with the combined use of various sensors.

Dual PPG and Oxygenation

Blood oxygenation includes a noise model and a physilogcal model. The noise model expects the SpO2 value to be relatively constant over the measurement period. The physiological model expects the SpO2 value to be within a range of values to be valid. For example, between 99% and 80%.

Referring to the flow chart shown in FIG. 6A, both PPG photodiode sensors A501 and A502 are positioned against the temple of the user. Both signals A602 and A606 are processed in parallel in the following sequence: The signal feeds into a FIR or FFT/IFFT filter (A603 respectively A607) removing noise from the data. The PPG-patient interaction model A511 of FIG. 5A (see additional explanation in FIG. 5B) is used to validate the measurements at this stage. The intensity of this signal is then normalized in A604 and A608 respectively. Both signals A604 and A608 flow into A609 performing a ratio between them as follows.

$$\text{ratio} = \frac{\frac{AC_{red}}{DC_{red}}}{\frac{AC_{IR}}{DC_{IR}}}$$

The terms are defined as follows: $AC_{red}$ is the alternating current red photodiode signal; $DC_{red}$ is the direct current red photodiode signal; $AC_{IR}$ is the alternating current infrared photodiode signal; $DC_{IR}$ is the direct current infrared photodiode signal. The outcome of A609 is merged in A610 with the SpO2 physiological model A612 (see additional explanation in FIG. 6C). The oxygenation values are shown to the user in A611 and/or stored into health records.

Optimal positioning of the PPG diodes is shown in FIG. 5B. When holding the device housing B501 against the temple, the PPG diodes A501 and A502 are in direct contact with the temple, with features blocking external light interference from A503 light sources/detector pairs. Due to hand instability and other small motions during the measurements, PPG diodes A501 and A502 may intermittently be perturbed by interfering ambient light, which will reduce accuracy of SpO2 predictions. The ambient light interference may also translate into saturation of the signals.

FIG. 6B illustrates an example of PPG signals B601 and B602 being respectively collected by PPG photodiodes A501 and A502 for various levels of SpO2 saturation. The Infrared (IR) PPG photodiode A502 generates signal B602 for the different saturation levels. The red photodiode A501 generates signal B601 for the different saturation levels.

Classic pulse oximetry algorithms normalize their input by dividing the alternating current (AC) component by the direct current (DC) component for each of the IR photodiode signal B602 and the red photodiode signal B601. They then determine the ratio between the red signals and the IR signals. The ratio is then used to calculate the SpO2 saturation through the relation shown in FIG. 6C.

Physiologically, SpO2 is a slow varying parameter for average, alert users, and may sometimes be considered to be constant during a measurement cycle. Other times, variability of SpO2 over time may be used in determination of respiratory rate. Oxygenation should be values between 96% and 99% in healthy individuals. If oxygenation drops to 92%, a user should use oxygen to increase the level. If oxygenation drops to 87%, is important that oxygen be used to avoid impairment. Impairment of mental functions can occur below 85%.

ECG+PPG and Blood Pressure
Calculation of Pulse Width Transit Time (PWTT)

The Pulse Width Transit Time (PWTT) includes a physiological model and a pair of noise models. The first noise model is to use an extracted PWTT value and a cross correlated PWTT value determined by different signal processing methods and fuse them together to determine a more precise and more stable value than that determined from peak detection alone. The second noise model is to obtain an extracted PWTT value by using measurements of peak detection through local estimations of PWTT that allows discarding parts of the signal without the peaks. The physiological model considers that the PWTT depends on the heart blood pressure and the vascular system.

Figure 7A:
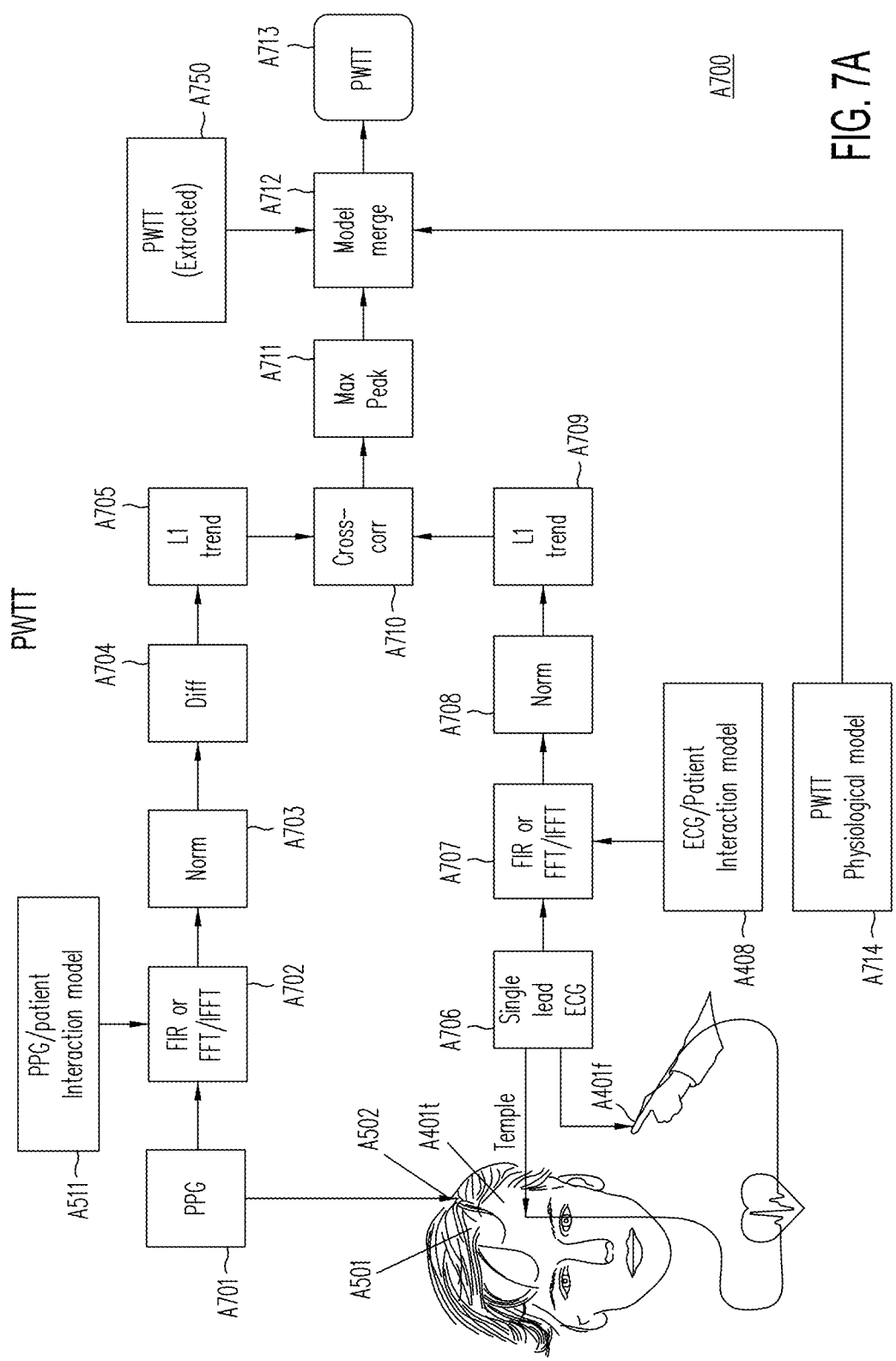
FIG. 7A is a flow chart illustrating an exemplary process of measuring the user's PWTT.

Referring to the flow chart shown in FIG. 7A, both PPG photodiode sensors A501 and A502 are positioned against the temple of the user. The signals from the PPG photodiode sensors A501 and A502 are processed by the PPG processor A701 to form the PPG signal A701 shown in FIG. 7B.

While the user holds the vitals signs scanner, the user's finger/thumb makes contact with an ECG electrode A401f of the ECG sensor. Concurrently in parallel with the PPG photodiode sensors positioned against the temple of the user, an ECG electrode A401t of the ECG sensor makes contact with the temple of the user. With these two connections, the electrical circuit with the ECG sensor is closed to generate an ECG signal S706 shown in FIG. 7B.

The PPG signal S701 is coupled into a finite impulse response (FIR) or fast Fourier transform (FFT/IFFT) filter A702 to remove noise from the data. The PPG-patient interaction model A511 (see additional explanation in FIGS. 5B, 5C and 5D) is then used to validate the measurements at this stage. The intensity of the PPG signal is then normalized in process A703 and flows to a first derivative (time gradient) filter A704 to form the differentiated PPG signal S704. The differentiated PPG signal S704 is further filtered by an L1 trend filter A705 forming the L1 trend differentiated PPG signal S705 shown in FIG. 7B.

Concurrently in parallel with the PPG signal processing, the A706 ECG signal is coupled into a FIR or FFT/IFFT filter A707 to remove noise from the desired data in the ECG signal. The ECG-patient interaction model A408 (see additional explanation with reference to FIGS. 4B, 4C, 4D, 4E) is then used to validate the measurements of the ECG signal at this stage. The intensity of ECG signal is then normalized by a normalizer A708 which is then coupled into an L1 trend filter A709 to generate the L1 trend ECG signal S706t shown in FIG. 7B.

The L1 trend ECG signal S706t from the L1 trend filter A709 and the L1 trend differential PPG signal S705 are cross-correlated by a cross-correlation function A710 to form a maximum ECG QRS complex signal S710. The outcome of the cross correlation, the maximum ECG QRS complex signal S710, is coupled into a peak detector to under a peak detection process A711 to calculate a raw PWTT value. A model merger process A712 occurs with the PWTT value and a PWTT physiological model A714 to validate and form the final PWTT values. Under a disclosure process A713, the final PWTT values may be shown the user and/or stored into health records. These final PWTT values may be referred to as cross correlation PWTT values.

Figures 1, 7B:
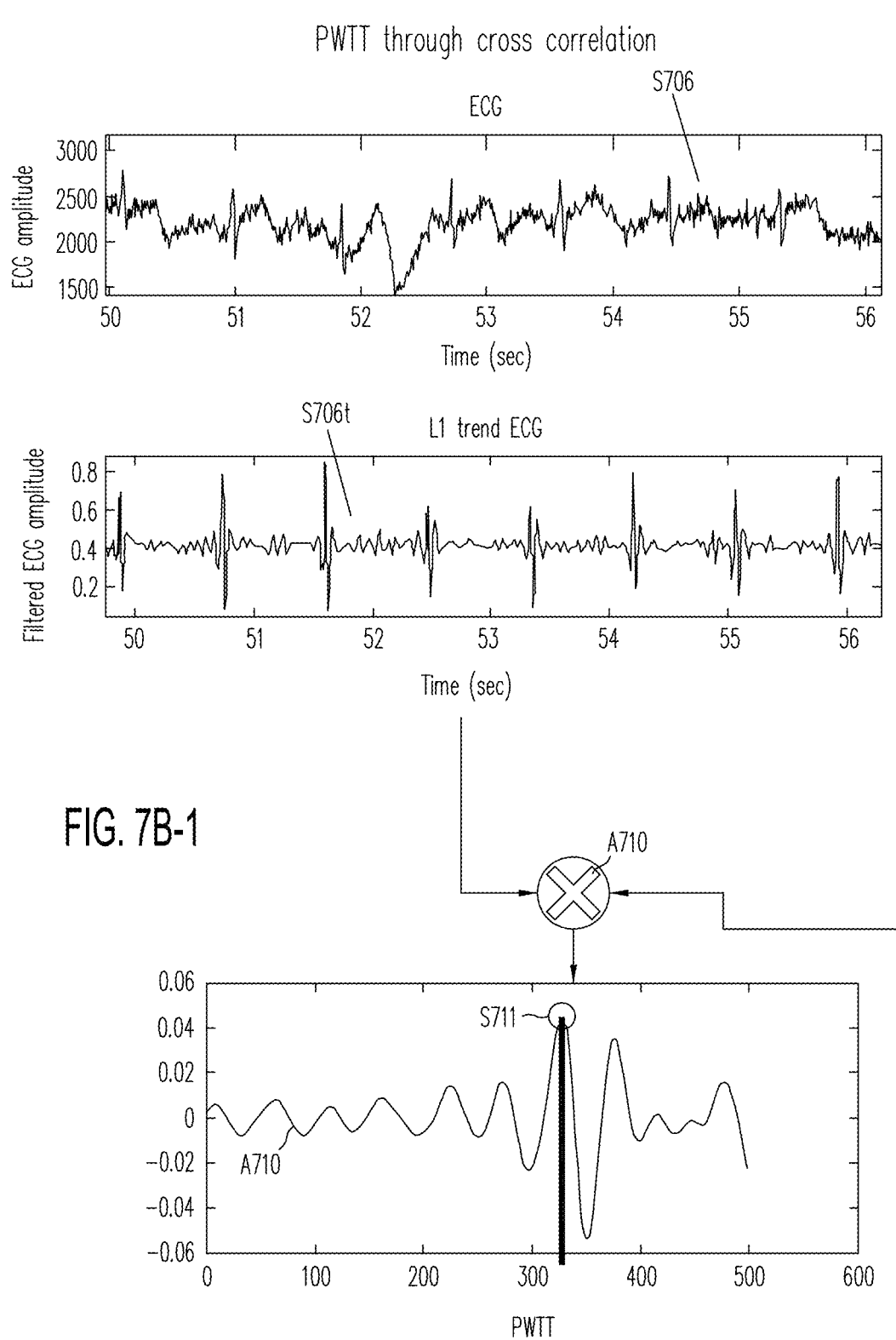
FIGS. 7B-7C illustrate differing exemplary pulse width transit time (PWTT) physiological models that may be merged together.

FIG. 7B provides a graphical illustration of the PWTT algorithm. The ECG signal S706 corresponds to a normalized ECG signal. This signal goes through the L1 trend filter to generate the L1 Trend ECG signal S706t. The L1 Trend ECG signal S706t is a first input into the cross-correlation function A710. In parallel, the PPG signal is normalized in A701 goes through a differential function A704 to finally traverse an L1 trend filter transforming into signal S705. The L1 Trend differential PPG signal S705 is a second input into the cross-correlation function A710. The signal resulting from the cross-correlation function A710 enters into the Max peak module A711 extracting the PWTT corresponding to the maximum peak of the cross-correlation.

Figures 1, 7C:
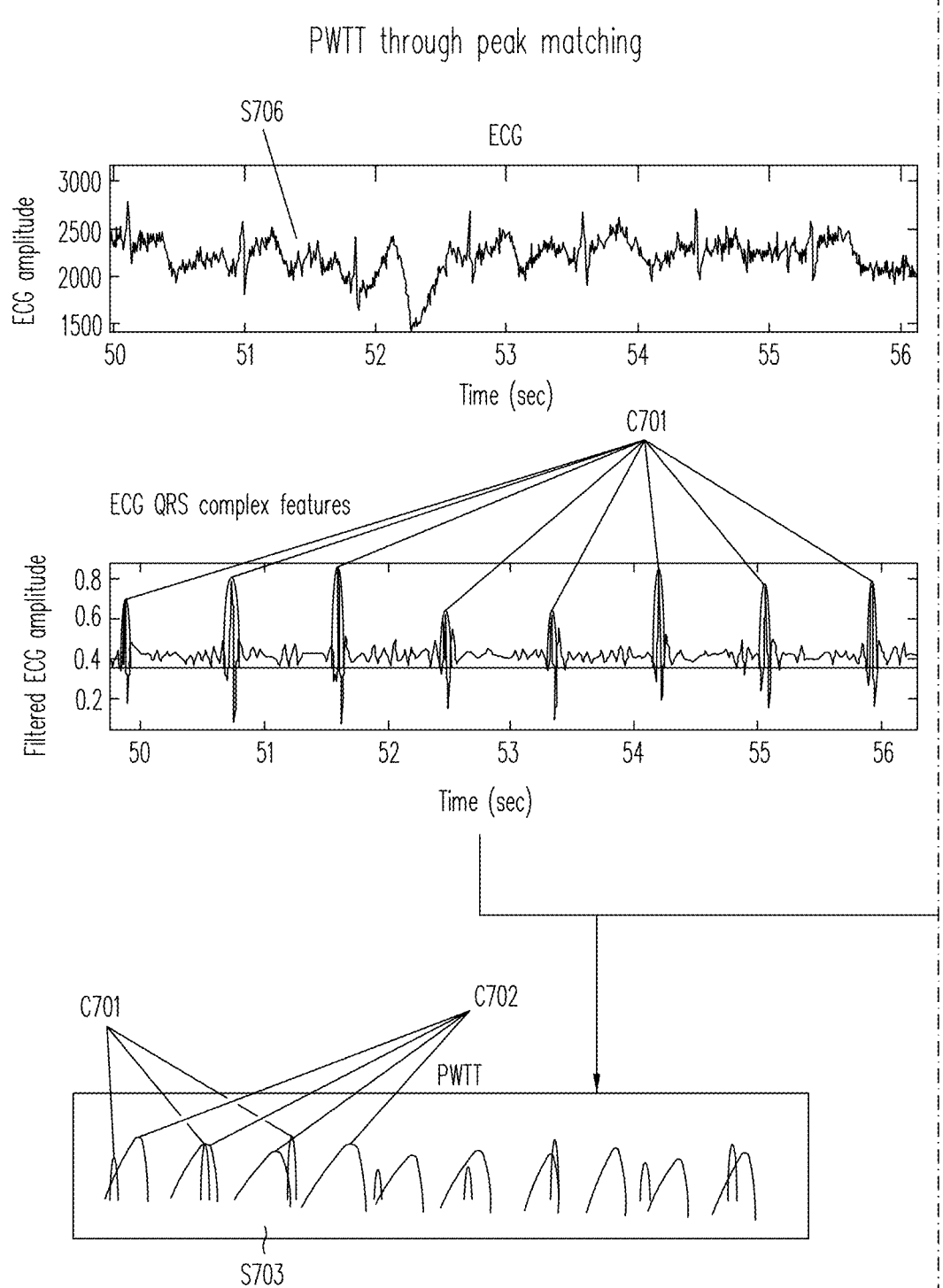

Referring to FIG. 7C, an extraction process A750 of calculating PWTT for a user is now described. An ECG extraction process extracts features from the ECG signal S706 to form an ECG QRS complex features signal. A PPG extraction process extracts features the PPG signal S701 to form a PPG features signal. A further peak extraction process is performed on ECG QRS complex features signal to extract the peak features ECG peaks C701 that correspond to the R feature of the ECG QRS complex. A further peak extraction process is performed on the PPG features signal to extract the peak feature PPG peaks C702 (or the rise time) associated with the PPG signal S701. These peak extraction features are based on local properties.

The calculation of the PWTT signal C703 is then based on the time difference between the ECG peaks C701 and the PPG peaks C702. The total error on the PWTT is the sum of the errors from peak extraction plus the errors in the peak alignment algorithm. However, the total error is averaged over the number of peaks in the observation window or time window of samples. These PWTT values may be referred to as extracted PWTT values.

In FIG. 7A, the PWTT value calculated by the extraction process A750 is coupled into the model merge module A712. The PWTT value calculated by the extraction process A750 can be combined with the PWTT calculated by the correlation process generated by the maximum peak detection process A711, as well as the PWTT physiological model A714. By using both PWTT computation models illustrated by the FIGS. 7B and 7C, a merging or fusion algorithm can mitigate the risks of error.

One merging or fusing approach to use in the model merge process A712 is to calculate PWTT based on the peak matching algorithm to get an approximate value, as well as to assess the quality of this signal based on the number of peak detections. Once this signal is validated, the cross-correlation algorithm can be used to perform a more precise determination and validate the overall PWTT result. A valid and accurate PWTT value is important in the computation of blood pressure.

Calculation of Blood Pressure

The calculation of blood pressure includes a physiological model and a noise model. The noise model is to use the sum of values for PWTT, pulse rate, heart rate, PPG spectral slope, PPG wave shape, ECG spectral slope, and ECG spread to improve signal quality. The physiological model considers that the systolic and diastolic blood pressure should be relatively constant over the measurement period with the values for systolic blood pressure being greater than the values for diastolic blood pressure.

Generally, blood pressure calculations by the vital signs scanner 100 with a signal processing model are described in U.S. patent application Ser. No. 14/641,303, filed on Mar. 6, 2015 by Max Little et al. and incorporated by reference. However, the blood pressure calculations can be further merged with an interaction model and a features extraction model to further improve the results of the blood pressure measurements.

Figure 8A:
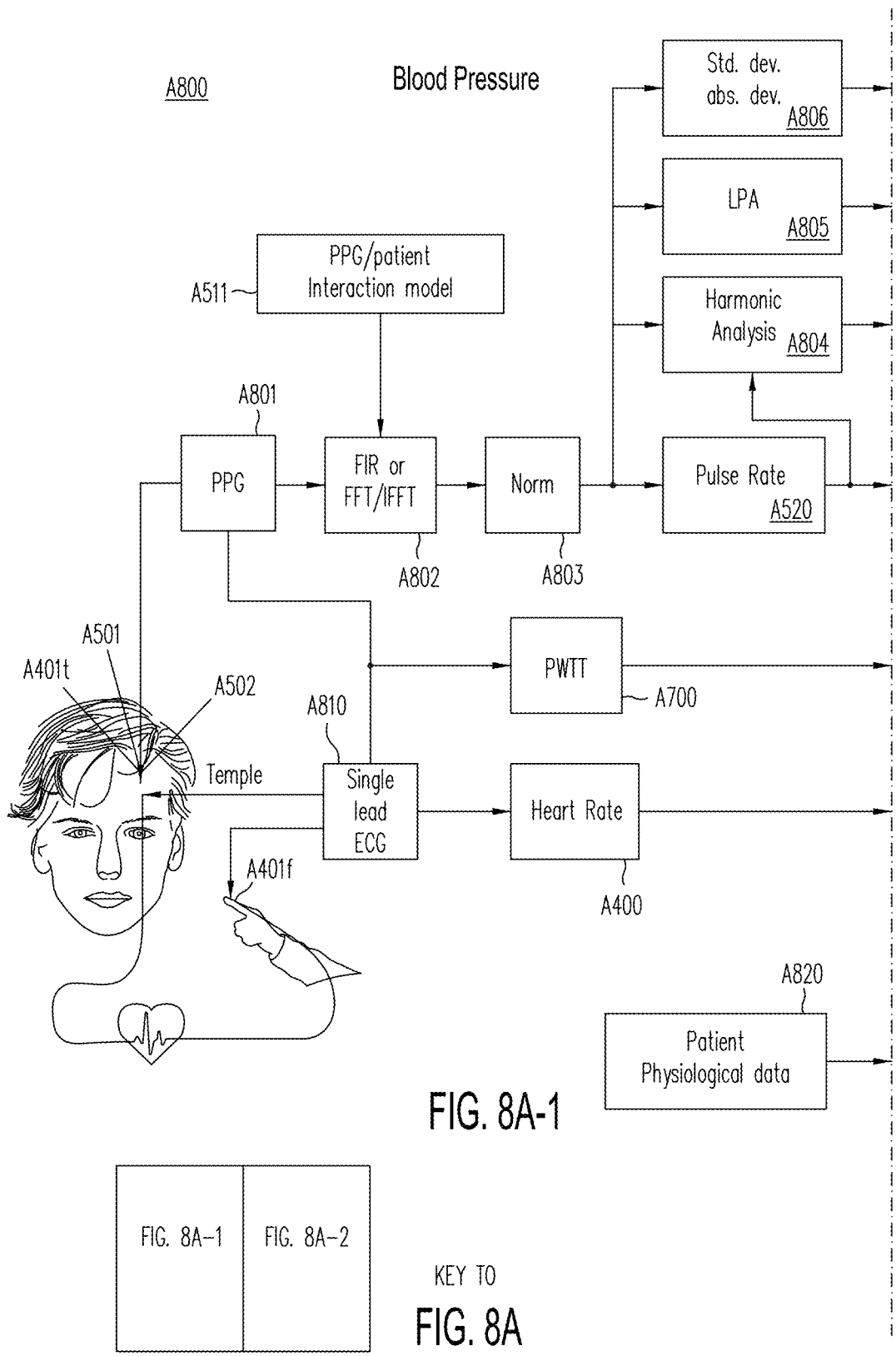
FIG. 8A is a flow chart illustrating an exemplary process of measuring blood pressure.
Figures 2, 8A:
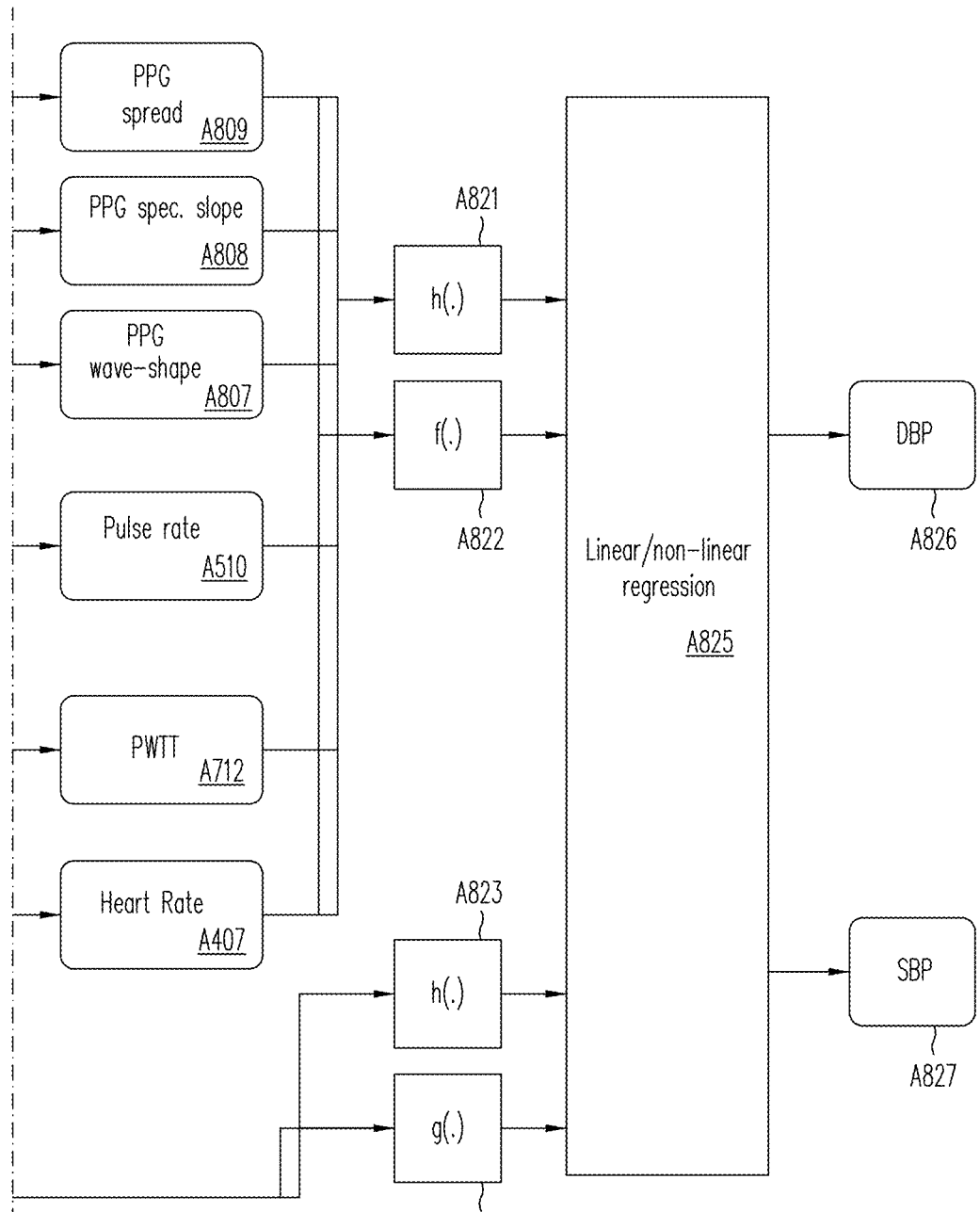

Referring now to the flow chart shown in FIG. 8A, blood pressure calculation process A800 is now described that includes a PPG/patient interaction model. Both PPG sensors A501, A502 are positioned against the temple of the user. The output signals of the PPG sensors A501 and A502 are processed during a PPG process A801 to determine and select a more reliable and perhaps less noisy PPG signal to undergo further signal processing.

Concurrently in parallel with the PPG signal capture process, ECG signals are captured during an ECG capture process A810 by the ECG sensor and its electrodes A401f, A401T making respective contact with a finger and temple of the user.

The ECG signal from the ECG capture process A810 is coupled into a heart rate signal processing algorithm A400 to generate a heart rate signal A407. In addition, the ECG signal from the ECG capture process A810 and the PPG signal from the PPG capture process A801 are coupled into the PWTT calculation process A700 to calculate the PWTT result A713. The PPG signal is also coupled into a FIR or FFT/IFFT filter A802 removing noise from the data. The PPG-patient interaction model A511 (see also FIGS. 5B and 5C and the description thereof) is used to validate the measurements at this stage. The intensity/amplitude of PPG signal is then normalized by a normalization process A803 to form a normalized signal A803 that flows in several directions.

The normalized PPG signal A803 is coupled into a pulse rate calculator A520 to generate the user's pulse rate A510. In addition, the normalized PPG signal A803 is coupled into a harmonic analysis A804 to produce the PPG wave-shape A807. Further, the normalized PPG signal A803 flows into a latent profile analysis (LPA) A805 to calculate the PPG spec slope A808. Further, the normalized PPG signal A803 feeds into a statistical module A806 to calculate standard deviation and absolute deviation, referred to as the PPG spread A809.

The calculated values A809, A808, A807, A510, A713 and A407 are then all coupled into a function f(.) A822 and a function h(.) A821. The function f(.) A822 and the function h(.) A821 apply mathematical transformations to the incoming data values to transform them into components of systolic blood pressure and diastolic blood pressure. The resultant component values of these transformations are coupled into the regression algorithm A825.

In parallel, patient physiological data A820 (e.g. age, sex, weight, size . . . ) is coupled into the function g(.) A824 and the function h(.) A823. The function g(.) A824 and the function h(.) A823 apply mathematical transformations to the incoming data values to transform them into components of systolic blood pressure and diastolic blood pressure. The resultant component values of these transformations are coupled into the regression algorithm A825.

Initially, in response to a calibration process, the user calibrates the regression algorithm A825 with a set of user parameters to weight the incoming components of systolic blood pressure values and diastolic blood pressure values that are then summed together to achieve known calibration systolic blood pressure values and diastolic blood pressure values. Subsequently, the user parameters for the regression algorithm A825 are used to calculate systolic blood pressure values and diastolic blood pressure values.

The resultant components of systolic blood pressure values and diastolic blood pressure values from the transformations are coupled into the regression algorithm A825. In response to the user's custom set of parameters and the resultant component values from the transformations, the regression algorithm A825 generates the outputs of diastolic blood pressure (DBP) A826 and systolic blood pressure (SBP) A827.

Figure 8B:
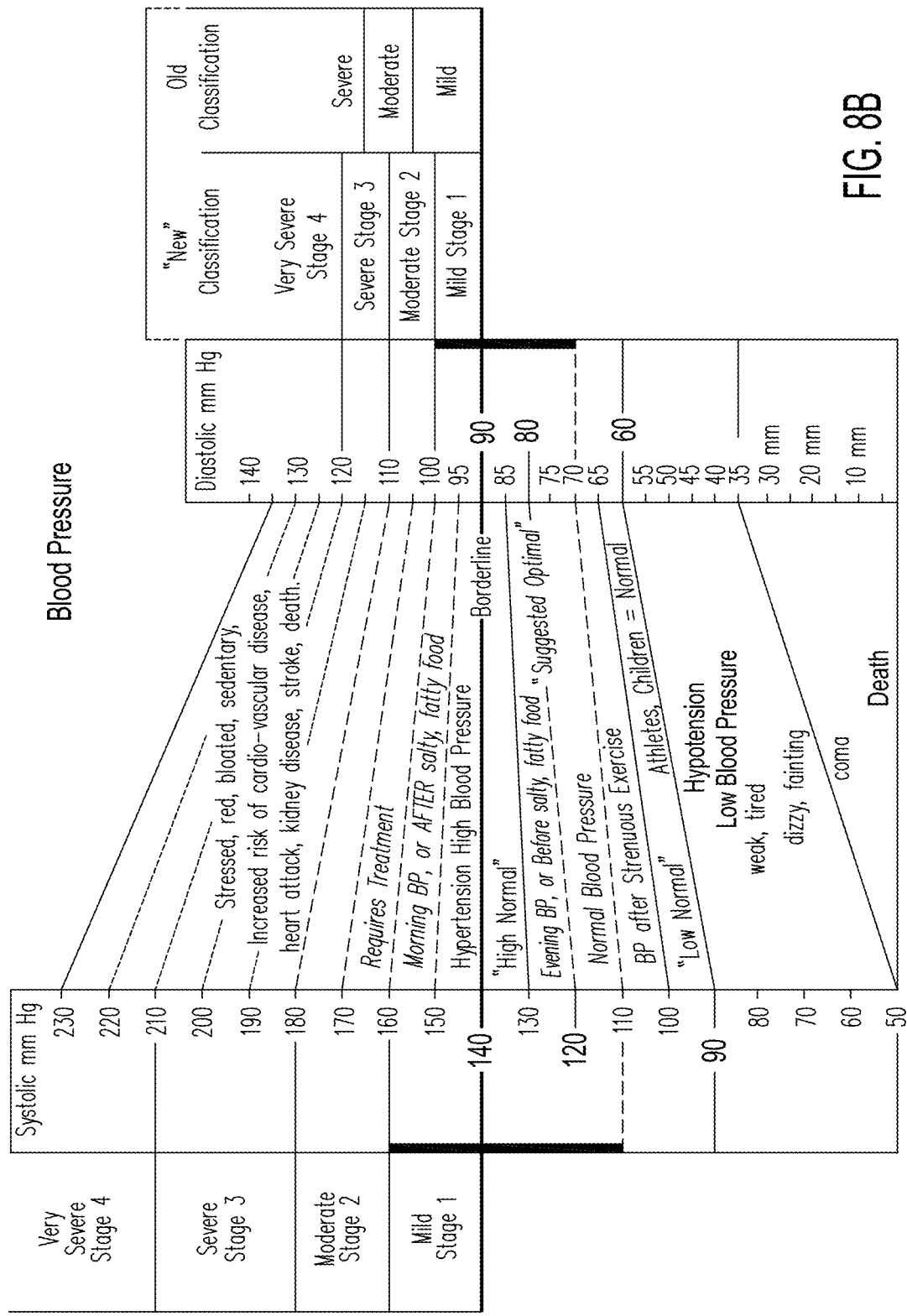
FIG. 8B illustrates an exemplary blood pressure physiological model.

FIG. 8B illustrates an exemplary blood pressure physiological model that may be used to validate blood pressure measurements determined by the process described in FIG. 8A. For example, the chart in FIG. 8B shows SBP in a range of 60-230 mm Hg and DBP in a range of 30-130 mm Hg. Blood pressure measurement outside that range may be considered suspicious.

Additional details relating to the process illustrated in FIGS. 8A-8B may be found in U.S. Provisional Patent Application Ser. No. 61/949,235 attached hereto as Appendix A and U.S. Provisional Patent Application Ser. No. 61/924,230 attached hereto as Appendix B, both of which are incorporated herein by reference.

ECG, PPG and Respiration Rate

Figure 9A:
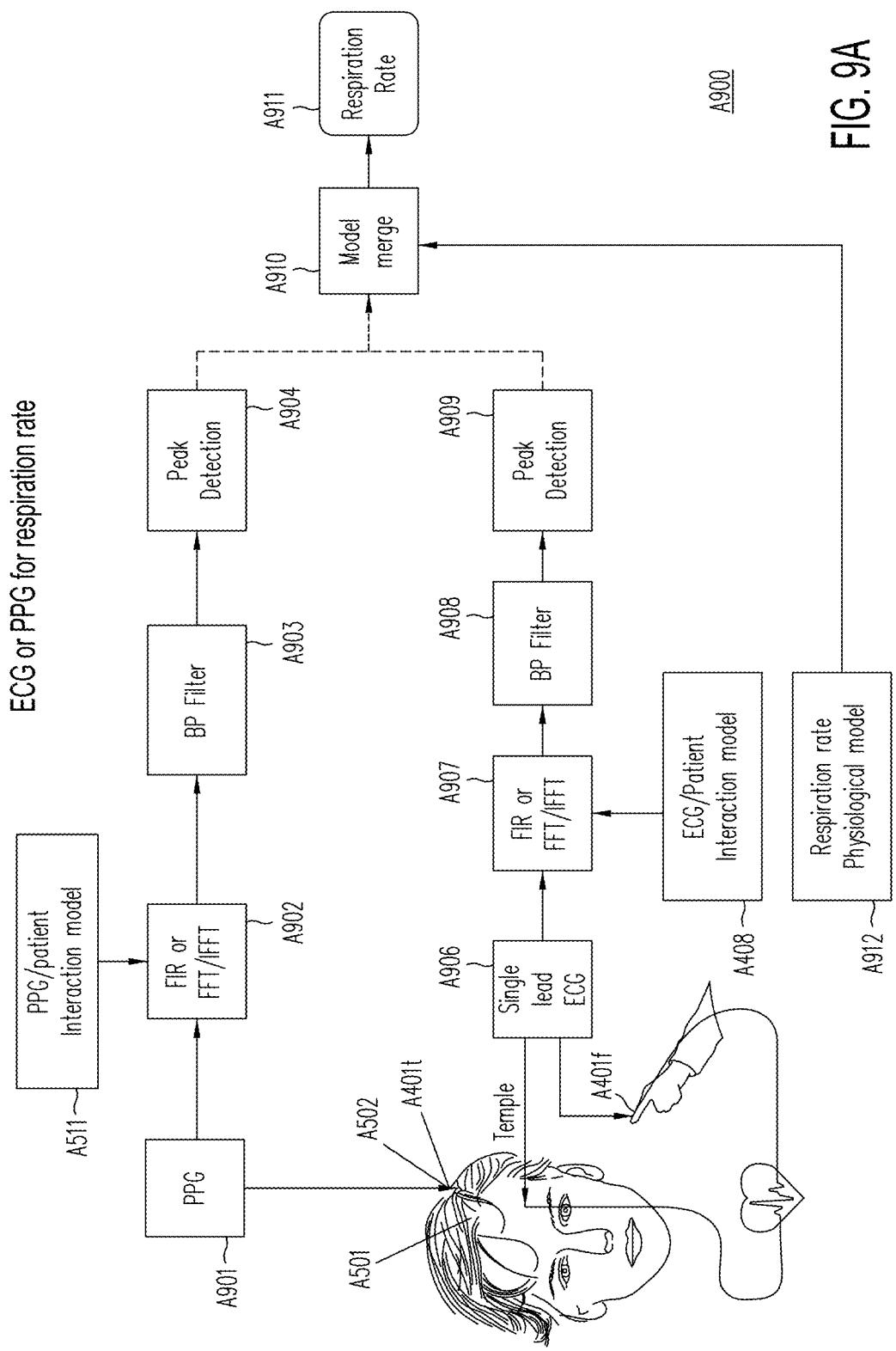
FIG. 9A is a flow chart illustrating an exemplary ECG/PPG based process of measuring respiration rate.

Reference is now made to the flow chart shown in FIG. 9A. Respiration rate can be extracted from either the PPG signal and/or from the ECG signal, with similar algorithms. A physiology model and a noise model are used during this process. The physiology model illustrates expect ranges of rates for adult, elderly living independently, elderly living in long term care, and a rage of respiration rates that suggest a medical condition (e.g., 10 beats per minute to 30 beat per minute). A first noise model uses the ECG peak amplitude and body noise as well as a determination that the ECG data is more stable that the PPG data during the same scan. A second noise model uses signal processing to look for patterns in sound signals around 20 Hz. A third noise model looks for accelerometer noises. A composition of acceleration is formed from three dimensions of acceleration and is compared with expected signals depending upon position of the vital signs scanner.

Using PPG to extract the respiration rate, sensors A501 and A502 are positioned against the temple of the user. Only the signal from one of the PPG sensors needs to be processed to determine respiration rate. The PPG signal S901 from the PPG sensor is coupled into a FIR or FFT/IFFT filter A902. The FIR or FFT/IFFT filter A902 removes noise from the PPG data signal.

The PPG-patient interaction model A511 (see additional explanation in FIGS. 5B, 5C and 5D) may be used to validate the PPG measurements from the PPG sensor. The resulting signal goes into a band pass filter A903 to remove low frequency components as well as high frequency component signals. The signal is then processed by a peak detection algorithm A904 that is responsive to the amplitude of the signal. The number of peaks in amplitude detected by the peak signal detector over a period of time is used to determine respiration rate.

In a similar manner, a single ECG sensor A401 with electrodes A401t and A401f closes an electrical circuit with the user's body between a finger/thumb coupled to electrode A401f and the temple of the user coupled to electrode A401t. The ECG signal A906 of the ECG sensor is coupled into a FIR or FFT/IFFT filter A907 to remove signal noise from the data signal.

The PPG-patient interaction model A408 (see additional explanation in FIGS. 4B, 4C, 4D and 4E) is used to validate the ECG signal measurements from the ECG sensor. The resulting signal goes into a band pass filter A908 to remove low frequency components as well as high frequency components from the ECG signal. The filtered ECG signal then undergoes a peak detection process with a peak detection algorithm A909 executed by a signal processor. In response to the amplitude of the filtered signal, the number of peaks detected over a period of time provides the respiration rate. More specifically, distribution of ECG peaks (R-waves) gives information about the heart rate as a function of time. Heart rate variability may be inferred from this function. Respiratory rate can be estimated from the heart rate variability.

The PPG extraction method or ECG extraction method, either used separately or together, causes signal A904 and/or A909 to enter into a model merge A910, comparing them to the physiological respiratory rate model A912. The physiological respiratory rate model A912 incorporates physiological limitations of respiration rates. For example the breathing rate of an average adult human is between 10 and 30 breaths per minute.

Figure 9B:
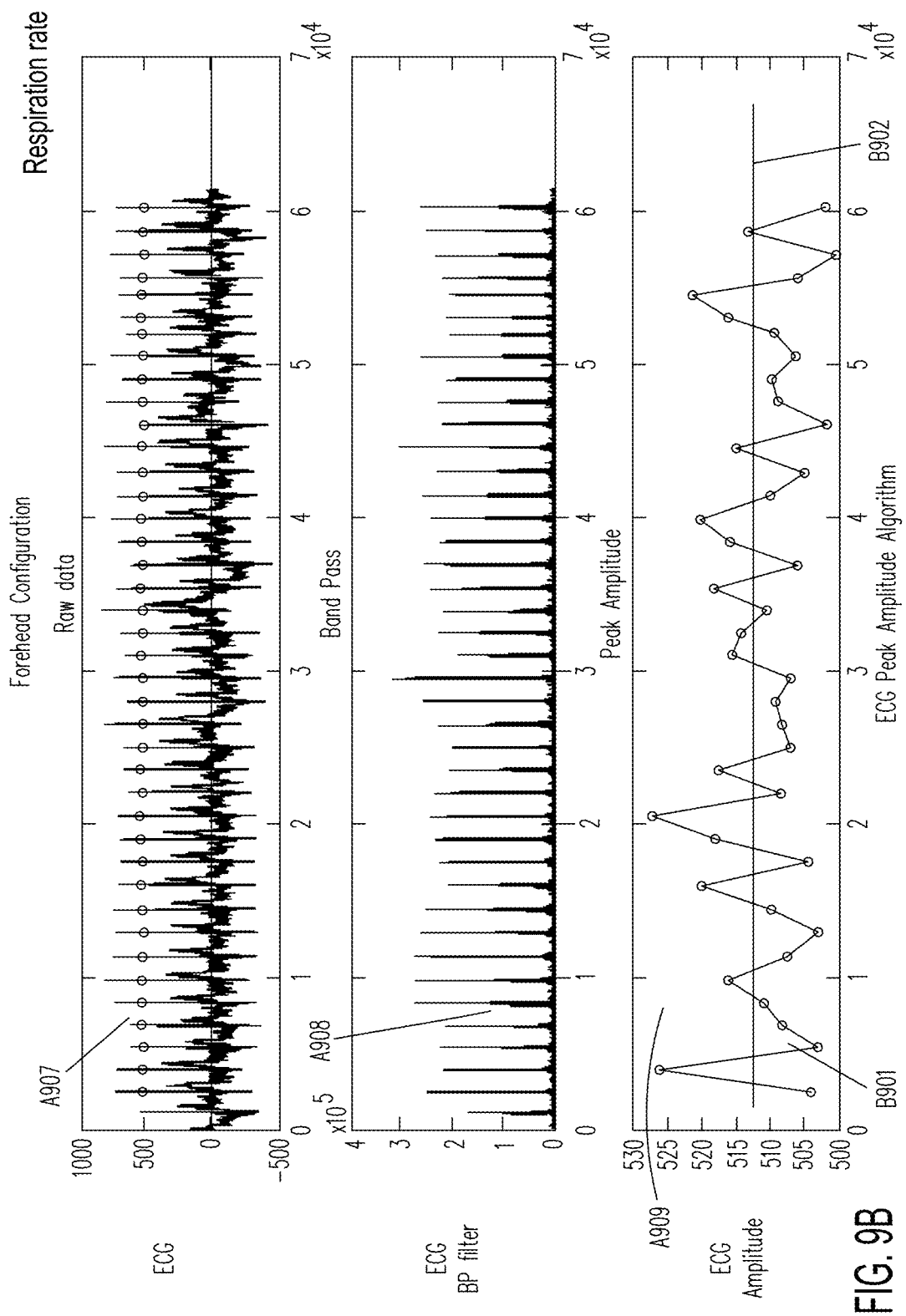
FIG. 9B illustrates an exemplary respiration rate physiological model.

FIG. 9B illustrates details of the exemplary ECG algorithm used to extract respiration rate. The ECG signal A906 feeds into a FIR or FFT/IFFT filter A907 to form the filtered signal S907. The filtered ECG signal S907 goes through the band pass filter A908 to generate the bandpassed ECG signal S908 shown in FIG. 9B. The bandpassed ECG signal S908 enters the peak detection algorithm A909 to generate the peak detected ECG signal S909. One way of performing peak detection is to set a threshold B902 and count the number of times the signal B901 extends beyond this threshold. Other algorithms known in the art can also be used.

Microphone and Respiration Rate

Figure 11A:
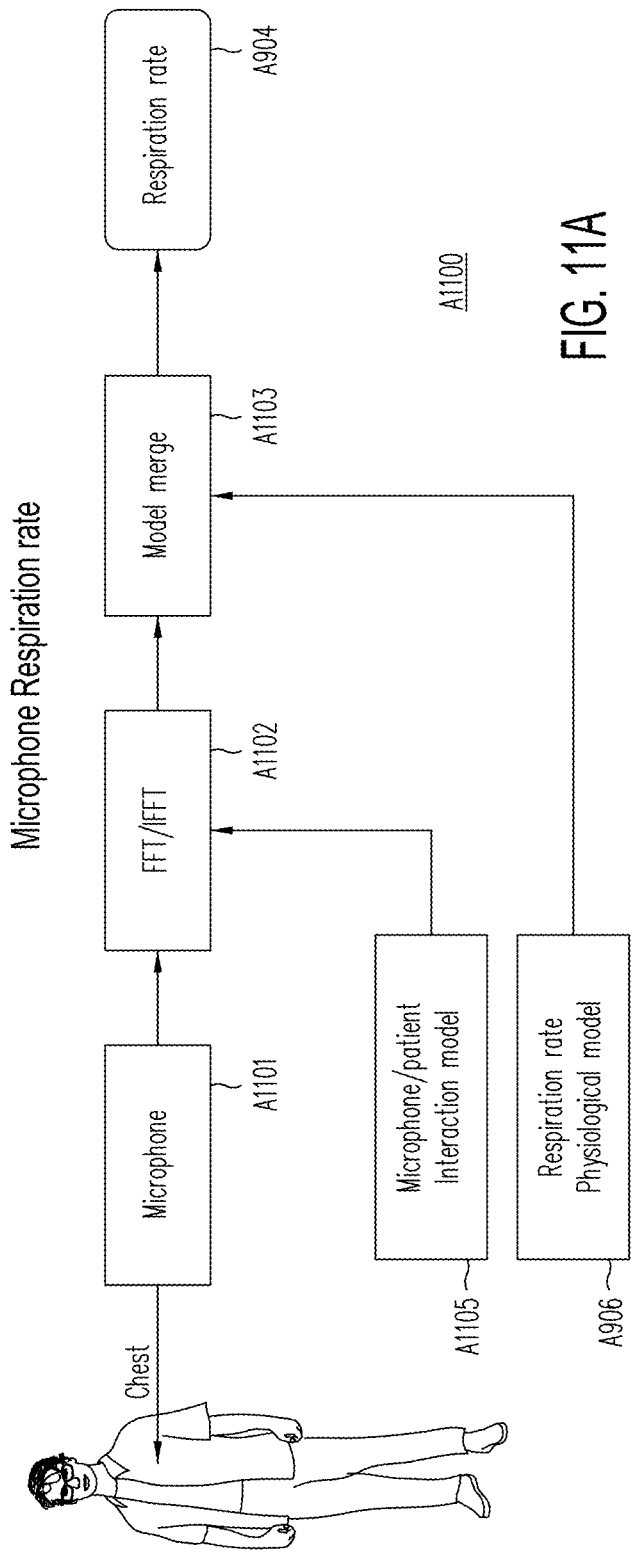
FIG. 11A is a flow chart illustrating an exemplary microphone-based process of measuring respiration rate.

Referring to the flow chart shown in FIG. 11A, microphone A1101 is pressed against the chest of the user to measure chest sounds. The output signal from the microphone A1101 is coupled into a signal processor A1102. The signal processor A1102 executes one or more signal processing algorithms, including an FFT/IFFT algorithm A1102 to remove some noise from a chest sound signal. The processor can then extract an initial respiration rate from the chest sound signal that has some noise removed.

Figure 11B:
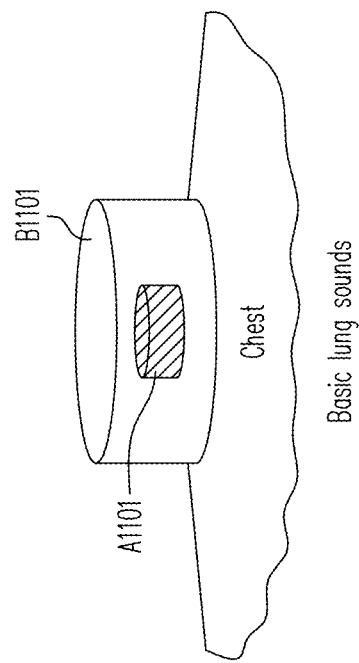
FIG. 11B illustrates an exemplary microphone to patient interaction model.
Figure 11C:
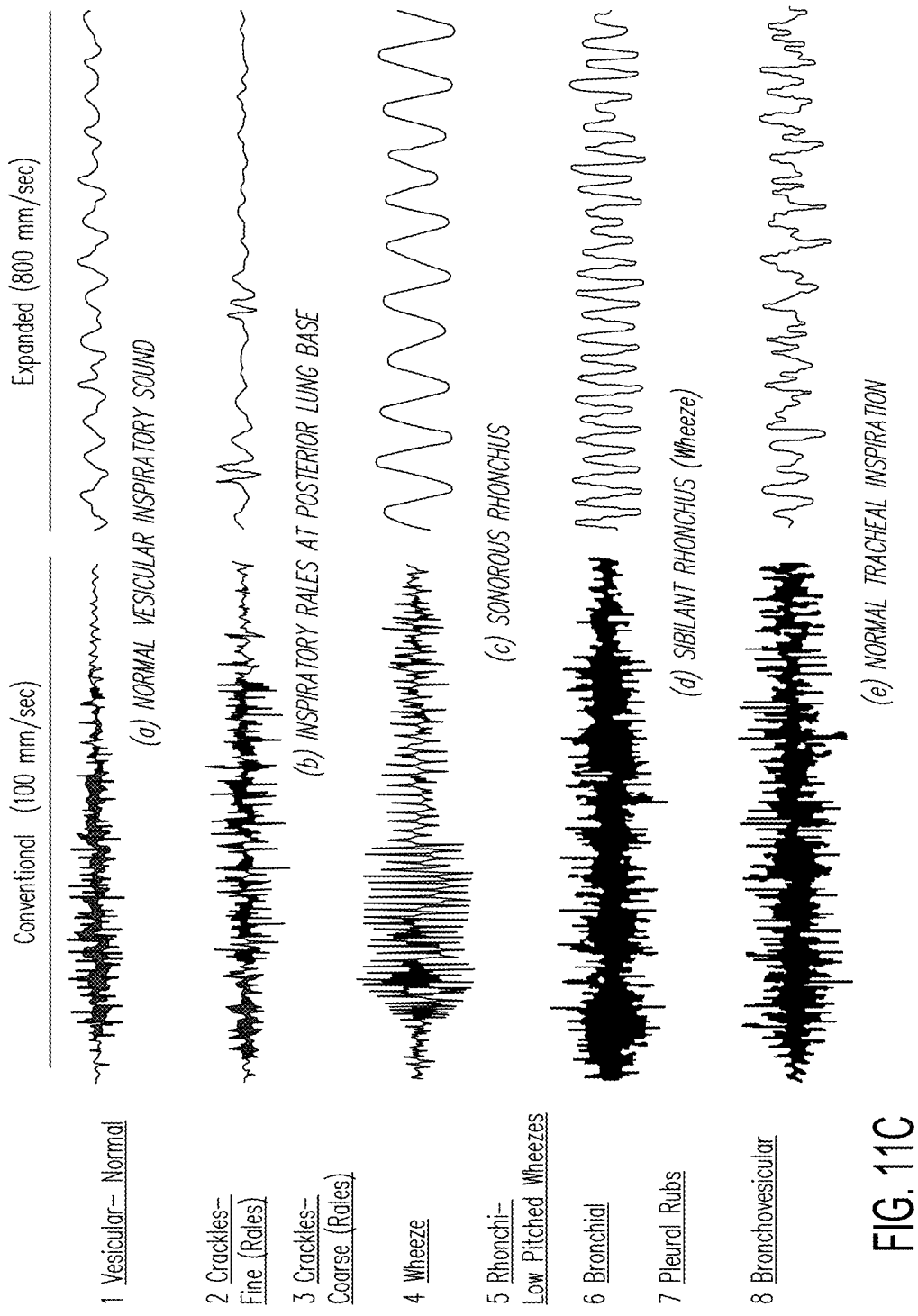
FIG. 11C illustrates an exemplary microphone physiological model.

The signal processor A1102 further receives a microphone-patient interaction model A1105 (see additional explanation with reference to FIGS. 11B and 11C). The microphone-patient interaction model A1105 includes an identified noise signal. The FFT/IFFT algorithm A1102 can use the microphone-patient interaction model A1105 to remove more noise (e.g., the identified noise signal) from the chest sound signal. The signal processor A1102 can then extract an intermediate respiration rate from the chest sound signal that has more noise removed. Note the microphone-patient interaction model A1105 may also be used by the signal processor A1102 to compare and recognize respiratory conditions in the data signal.

After noise reduction, a model merge A1103 includes a validation process that compares the intermediate respiration rate is compared to a physiological respiration model A906. The comparison includes checks for physiological validity of the intermediate respiration rate. The physiological respiration model A906 includes an ECG signal captured from an ECG sensor (see additional explanation described with reference to FIG. 9B). If determined to be valid, the intermediate respiration is accepted as the overall respiration rate A904. The overall respiration rate A904 is presented to the user and/or stored into health records on a storage device.

FIG. 11B illustrates the positioning of the device on the user's chest. The housing of the vital signs scanning device B1101 is pressed up against the user's chest. The microphone A1101 in the vital signs scanning device B1101 records the lung sounds around the chest. If the user is lying on their back, the vital signs scanning device B1101 may simply be laid onto the user's chest.

FIG. 11C illustrates typical lung sounds captured by microphones. These lung sounds are classified into well established sound categories, such as vesicular, crackles, wheeze, rhonchi, bronchial, pleural rubs, and bronchovesicular sounds. It is known how to analyze each of these sounds to extract respiration rates from a signal.

A simple exemplary process for determining respiration rate is shown in FIG. 10A. A microphone A1101 is placed at the user's chest and a sound recording is made into a sound recording system A1001. The recordings are analyzed and respiration rates are extracted.

Accelerometer and Respiration Rate

Referring to the flow chart shown in FIG. 13A, a three dimensional accelerometer A1301 in a housing is pressed against the chest of the user to measure chest motion as the user breathes. A 3D accelerometer output signal from the three-dimensional accelerometer A1301 is coupled into a signal processing module A1302. The signal processing module A1302 removes some noise from the chest motion signal (e.g., by applying FFT/IFFT). The processing module A1302 also detects peaks (e.g., estimates peak-to-peak time intervals) in the chest motion signal by using a moving average peak detector. The processor module A1302 can use the detected peaks to extract an initial respiration from the chest motion signal.

The signal processing module A1302 further receives a second input (e.g., noise signal) from an accelerometer-patient interaction model A1305. The accelerometer-patient interaction model A1305 is further described herein with reference to FIGS. 13B and 13C.

The peak detection signal from the signal processing block A1302 is coupled into a peak-to-peak interval estimator A1303 that performs more peak-to-peak time interval detection. The peak-to-peak interval is a measurement that corresponds to the intermediate respiration rate of the user.

A comparator A1304 compares the measured peak-to-peak time intervals against a physiological respiration model A906. The physiological respiration model A906 is described with reference to FIG. 9B. The comparator A1304 checks the measured peak-to-peak time intervals for physiological validity. If the measured peak-to-peak time intervals are physiologically valid, at process A904, the overall respiration rate is shown to the user on a display device and/or stored into a storage device with a health records database.

FIG. 13B illustrates positioning the vital signs scanning device B1101 on the user's chest. The housing of the device B1101 is simply pressed against the chest of the user. The 3D accelerometer A1301 in the device B1101 records chest motion. If the user is lying on their back to obtain a better reading, the device may simply be laid on the chest of the user.

FIG. 13C illustrates waveforms of an exemplary accelerometer-user interaction model. The waveform signal C1301 represents the normal or perpendicular motion of the chest wall while breathing. The model represents the expected normal motion of a user's chest as he/she breathes. However, the frequency of motion of the user's chest still needs to be determined. Chest movement is measured by the accelerometer A1301. The signal generated by the accelerometer A1301 as a result of the chest movement detects, for example a vector component normal to the chest, or a vectorial sum of the X, Y, and Z axis of accelerations of the chest. The peak detection algorithm A1302 executed by the signal processor in response to the model A1305, extracts the breath inhalation frequency of the user over time. The signal processor further analyses the peak-to-peak time intervals in the breath inhalation frequency and converts it using the respiration rate algorithm A1303 into a measured respiration rate. The comparison algorithm A1304 compares the measured respiration rate to the respiration rate physiological model A906 to be sure the measured respiration rate is valid, before generating the output respiration rate A904.

The raw recorded data of the chest movement could be analyzed later in some cases. If this is the case, a simpler embodiment such as shown in FIG. 12A may be used to record and store chest movement. The vital signs scanning device B1101 with the three dimensional accelerometer A1301 is placed against the chest of the user. The output signals from the accelerometer A1301 are recorded over time by a motion recording system A1201. The recorded output signals can be stored in a storage device for later analysis and comparison.

Noise and Multiple-Sensors
Temple Measurements

By design, the system described herein performs multiple measurements in parallel. Since sensors are all closely positioned in the same housing of the vital signs scanner 100, they receive similar noise, such as vibrations or motion.

Figure 14:
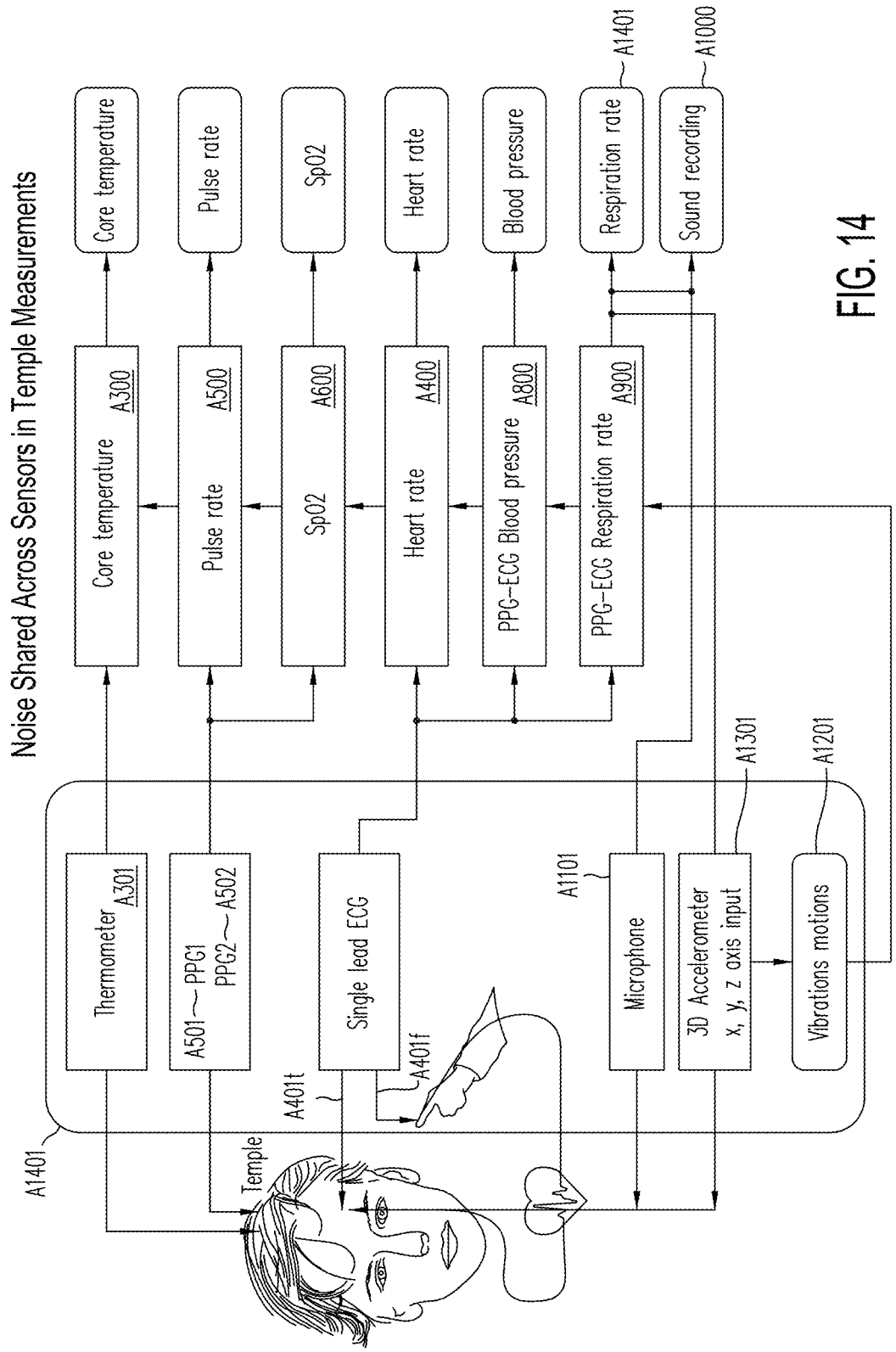
FIG. 14 is a block diagram illustrating noise shared across sensors in temple measurements.

Referring now to the flow chart shown in FIG. 14A, a housing or enclosure A1401 of the vital signs scanner includes a plurality of sensors, including an accelerometer A1301. The accelerometer A1301 in the housing records the vibrations and motions A1201 of the scanner 100. The vibrations and motions A1201 of the accelerometer may be shared with the other sensors.

Some sensors, like the microphone A1101 are directly perturbed by vibrations since sounds and vibrations are both mechanical vibrations. As such, corrective methods like noise subtraction and cross-correlation may be used.

The other sensors, thermometer A301, PPG sensors A501 and 502, ECG (401t A401f) are indirectly perturbed by vibrations. They do not directly react to vibrations or motion, but the quality of their signal depends on the sensor/patient interaction model.

In the case of the thermometer, vibrations have a lesser effect due to the constant air gap maintained by mechanical design between the sensor and the temple. However relative motion between the temple and the sensor may show differences if the sensor moves over the temporal artery, because blood in the temporal artery is warmer than other blood in the temple.

For PPG and ECG sensors, the smallest vibrations may generate significant errors. The ECG signal from the ECG sensor shows noise pollution spikes in response to a small vibration. The PPG signal from the PPG sensor shows signal saturation when external light breaks the seal between the device and the temple.

An example of an improvement gained from using multiple sensors is an algorithm for the respiration rate that combines the results of accelerometer A1301, microphone A1101 and PPG-ECG (A501, A502, A401t and A401f) sensor data. The fusion algorithm initially considers the results of the accelerometers measuring the chest motion since this is a simple sinusoidal motion in a single dimension. Maximum chest motion (highest speed) corresponds to the peaks in the breathing action. Minimum chest motion (lowest speed) corresponds to full inhalation and full exhalation. This provides the initial determination of the respiration rate, with the precise moments corresponding to maximum inhalation time point $t_{in}$ and maximum exhalation time point $t_{ex}$. By providing the time points $t_{in}$ and $t_{ex}$ to the microphone respiration rate algorithm and to the PPG-ECG respiration rate algorithm, it can predict alternate measures $t'_{in}$ and $t'_{ex}$ for maximum inhalation time point and maximum exhalation time point to verify the prediction for respiration rate. The final determination of respiration rate A1401 may be a combination of the respiration rates determined from the measures for maximum inhalation time point $t_{in}$ and maximum exhalation time point $t_{ex}$, and alternate minimum inhalation time point $t'_{in}$ and alternate maximum exhalation time point $t'_{ex}$.

Other vital signs measurements such as blood pressure (BP), heart rate (FIR), pulse rate (PR), blood oxygenation (SpO2), and core temperature are also improved by recognition of a noise signature in the signals from the accelerometers. The noise signature in signals from the accelerometer can be transmitted to a user interface for the scanner 100 to provide feedback to the user. The user interface, in response to the noise signature, can encourage the user to improve the grip and positioning of the scanning device. For example, detection of device oscillations may mean the device needs to be pressed a little harder against the user's temple. Another possible improvement in signal quality may be made detecting steady motion of the scanner 100. A steady motion in the scanning device 100 can cause some measurements, such as temperature from the temperature sensor, to capture less accurate data and generate less accurate results. In response to motion of the scanning device being sensed by the accelerometer, a message may be presented to the user by the user interface to hold scanner steady.

Training sessions can also be provided by the user interface software application of the vital signs scanner 100. A training session can show where the scanner 100 is to be positioned against the body. A training session can be used to show how the scanner 100 is to be gripped. A training session by the user interface can propose exercises to address common mistakes that may be made using the device. During these training sessions, sounds may be emitted by vital signs scanner and its user interface to train users in reaching the optimal use of the device. After training, the device can be used to statistically collect accelerometer measurements to assess usage improvement of the vital signs scanner by the user and pinpoint opportunities for further improvement in its use.

Chest Measurements

For chest measurements the device performs two measurements in parallel. Since the sensors are closely positioned in the device housing they share noise, in particular the vibrations and motion.

Figure 15:
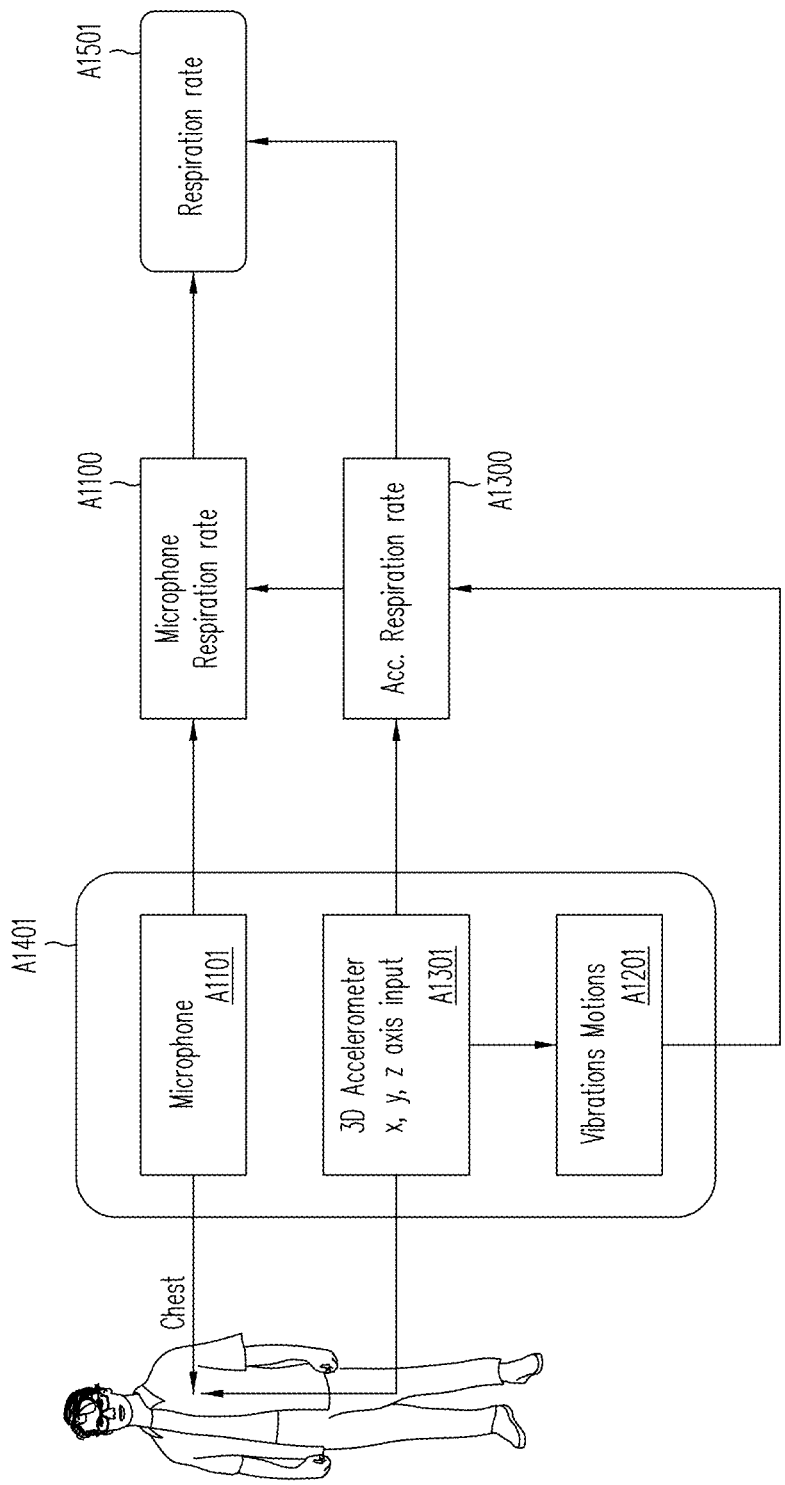
FIG. 15 is a flow chart illustrating chest measurement with the noise shared across sensors in chest measurements.

Referring now to the flow chart shown in FIG. 15A, the device enclosure A1401 is represented by a shape containing all sensors. The accelerometer A1301 records all the accelerations of the body enclosure, whereas the microphone A1101 records all the sounds. Since both are mechanical vibrations, they can be used to correct each other and provide more accurate respiration rates.

Combining the results of the accelerometer and microphone is another example of improving the algorithm for determining the respiration rate. First, the results of the accelerometer measuring the chest motion are considered because this is a simple sinusoidal motion in a single dimension. The respiration inhalation and the exhalation correspond respectively to the maximum and the minimum in the chest motion. This provides the initial determination of the respiration rate, with the precise moments corresponding to maximum inhalation $t_{in}$ and maximum exhalation $t_{ex}$. By providing $t_{in}$ and $t_{ex}$ to the microphone respiration rate algorithm, simple verification techniques on the sound track can be made, instead of making more complex determinations. The final determination of respiration rate A1501 may come either from the microphone A1100, or from the accelerometer A1300.

If the user takes measurements while lying down, the device may be positioned on their chest. This reduces signal pollutions as the accelerometers are just sensing the up and down chest motions and not movement from the user swaying, fidgeting, etc.

Sensor Fusion

Temple Measurements

The vital signs scanner 100 concurrently performs multiple measurements in parallel with multiple sensors during a measurement period under control of the same processor. Due to these parallel operations over the same timeline, some measurements from one or more sensors may be used to correct/validate others and improve the quality of the vital sign measurements generated by the device.

Figures 1, 16:
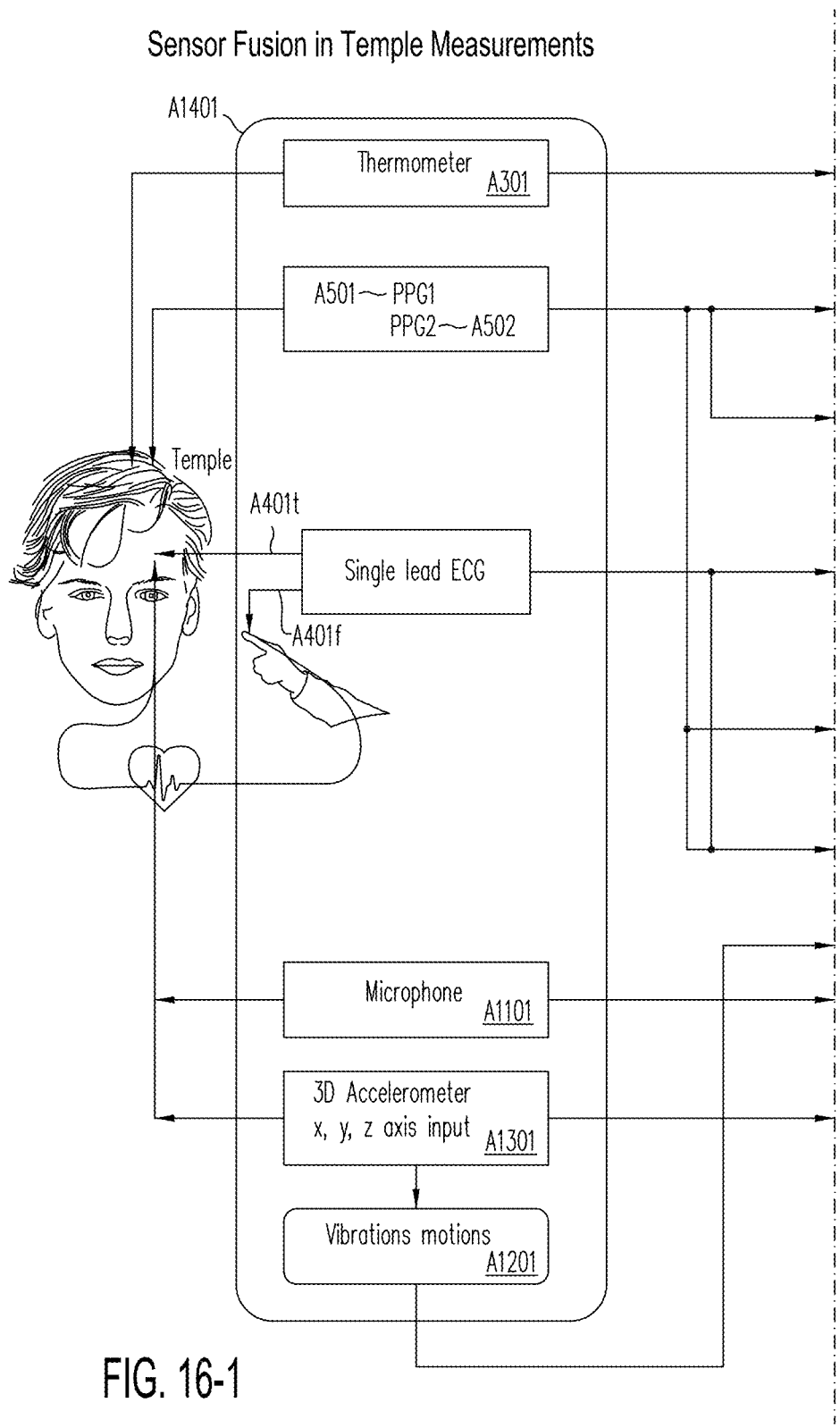
FIG. 16 is a block diagram illustrating sensory fusion across sensors in temple measurements.
Figures 2, 16:
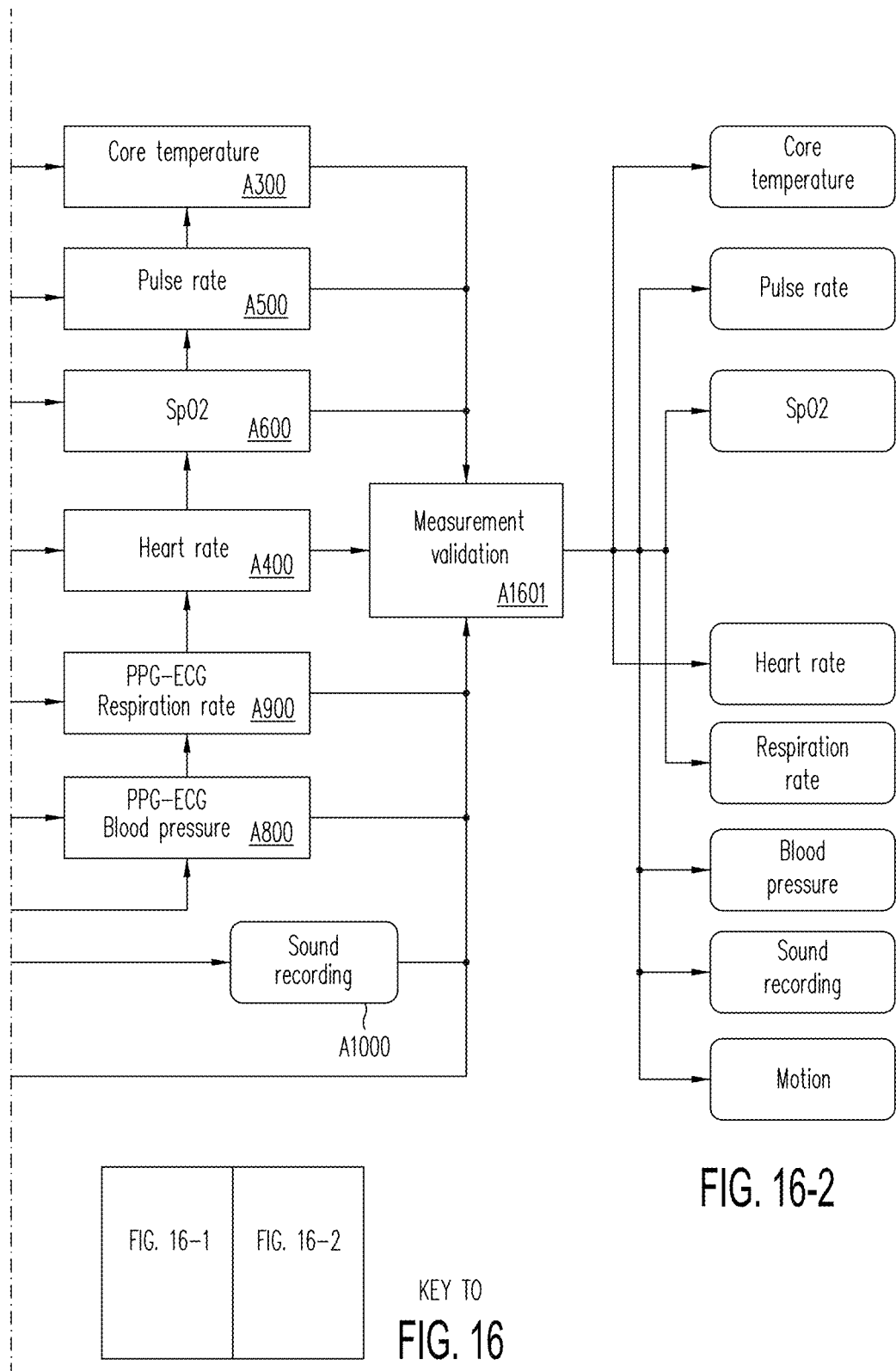

Referring now to the flow chart shown in FIG. 16A, the device housing A1401 is represented by a shape containing multiple sensors. An accelerometer A1301 records accelerations of the housing, which can be shared with other sensors. The sensor data or signals from the multiple sensors in the vital signs scanning device 100 may be fused together, perhaps with other data as well, to improve measurement quality of the vital signs.

The thermometer A301 with its signal processing A300, the PPG sensors A501 and 502 are connected to all of the following—pulse rate A500, SpO2 rate A600, blood pressure A800 and, respiration rate A900. The ECG sensor with single lead ECG with an electrode A401$t$ on the temple and an electrode A401$f$ on the finger/thumb is connected to all of the following—heart rate A400, respiration rate A900 and, blood pressure A800. The sensor data from the microphone A1101 and the sensor data from the accelerometer A1301 captured concurrently may be fused together by a signal processor to generate a higher quality of measurement of respiration rate A900 for a user.

Since the measurements taken by the sensors are concurrently performed in parallel, one or more signals of sensor data may be used to validate other data or vital sign measurements in a measurement validation process A1601. A data fusion algorithm may be used to fuse different data together to validate or enhance the quality of the vital sign measurements. A fusion algorithm, for example, receives a measure of respiration rate from three sources—PPG-ECG, microphone, and accelerometers—and compares them to assess the validity of their measurements. The different measures of respiration rate from each may be weighted based on a perceived quality in their data. For example, if the signal from the accelerometers used to determine respiration rate was not too noisy, its signal and measurement may be given greater weight in a weighted sum of the outputs. If the respiration rate determined from fusing PPG-ECG sensor data is comparable to the respiration rate determined from the accelerometer and microphone, the fusion algorithm may raise the confidence of both ECG and PPG and give it a greater weight in the weighted sum of the outputs. With the respiration rate from fusing PPG-ECG sensor data being comparable to the respiration rate determined from the accelerometer and microphone, the fusion algorithm may also raise the confidence of their use in the blood pressure calculation process A800 by the signal processor.

Another example of a fusion algorithm to fuse different data from different sensors is to compare the pulse rate and heart rate that has been determined in the signal processing processes A500 and A400. In most cases, these values are very similar. With similar pulse rate and heart rate being determined in the respective processes A500 and A400 by the signal processor, the trust of the ECG sensor data and PPG sensor data can be raised and weighted more heavily due to the sensor data being of higher quality. Because ECG and PPG are also used to determine the vital signs of blood oxygenation and pulse rate, and their quality of sensor data is determined to be higher, the trust in the vital sign measurements for SpO2 and pulse rate determined in signal processing steps A600 and A500 are higher.

Motions A1201 of the scanning device 100 can be used to validate and invalidate sensor data and the vital sign measures. For example, core temperature determined from the sensor data measured by the temperature sensor A301 can be trusted when there is little motion of the scanning device 100 near the temple of the user. If the motion A1201 sensed by the one or more accelerometers A1301 is nearly zero, the core temperature determination is higher in quality and can be validated by the lack of motion. If the motion A1201 sensed by the one or more accelerometers A1301 is substantial, the core temperature determination is of lower quality and invalidated during the measurement validation process A1601.

The measurement validation algorithm and signal processing process A1601 may validate the data in an all or nothing mode in some cases. All vital sign measurements may be invalidated in some cases. For example, if a plurality of sensors capture no data, or have constant data with no change, the scanner 100 may be improperly and so all vital sign data should be considered to be of low quality and perhaps discarded. Alternatively in other cases, the measurement validation algorithm and signal processing process A1601 may partially validate the data, updating only the validated vital sign measurements and setting blank or zero values for the output vital sign values for invalidated vital sign measurements.

Chest Measurements

For vital signs measurements made at a user's chest during a measurement period, the vital signs scanning device 100 may concurrently perform two measurements in parallel. At the user's chest, sound measurement or capture of sounds (by microphone A1101) and the measurement or capture of accelerations (by accelerometers A1301) may be concurrently performed. With the sensors contained within the same housing of the vital signs scanning device 100, the sensors may be submitted to similar stimuli but capture it in different manners. Hence, the signals of the sensors, including sound signals captured by the microphone, share the same timeline. Accordingly, features of the sound in a sound signal can be compared, time-wise to the features of a motion signal captured by the accelerometers, for example.

Figure 17:
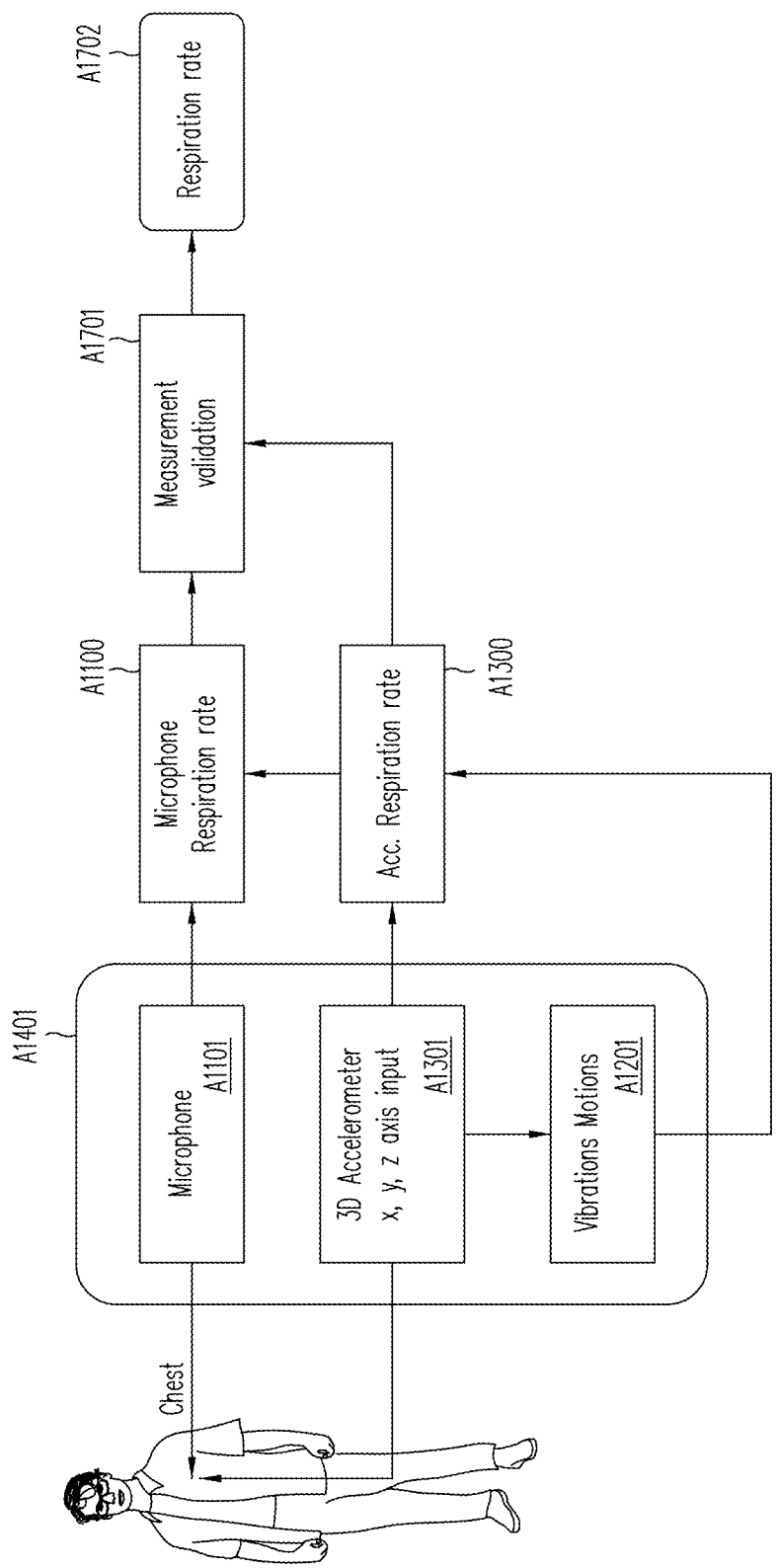
FIG. 17 is a flow chart illustrating the sensory fusion process for sensors in chest measurements.

Referring now to FIG. 17A, a fusion algorithm for the respiration rate combines the results or signals of an accelerometer and a microphone, for example. The results of the accelerometers measuring the chest motion A1300 are initially considered, because their model is a simple sinusoidal motion in a single dimension. The respiration inhalation and the exhalation correspond respectively to a maximum or peak chest position and a minimum or lowest chest position. This provides the initial determination of the respiration rate, with the precise moments in time of the peak chest position and the lowest chest position corresponding to a maximum inhalation time $t_{in}$ and maximum exhalation time $t_{ex}$.

The time points of maximum inhalation time $t_{in}$ and maximum exhalation time $t_{ex}$ are coupled into the microphone respiration rate algorithm A1100. The microphone respiration rate algorithm A1100 can use simple verification techniques with the sound track of the recorded sounds using the maximum inhalation $t_{in}$ and maximum exhalation $t_{ex}$, instead of making more complex determinations. A measurement validation A1701, including a final validation algorithm, can be implemented by checking that the microphone determined respiration rate A1100 is equal or close enough to the accelerometer respiration rate A1300 determined from the accelerometers A1301 to validate the displayed respiration rate A1702. If the accelerometer respiration rate A1300 and microphone determined respiration rate A1100 are substantially different then the displayed respiration rate A1702 may be set to a blank value.

If the user takes measurements while lying down, the vital signs scanning device 100 may be positioned on their chest to measure respiration rate. This reduces signal pollutions as the accelerometers are just sensing the up and down chest motions, and avoid measuring other user movements, such as from the user swaying, fidgeting, etc.

Vital Signs Scanner Detail

The vital signs scanner 100 was introduced by FIGS. 1 and 2A-2B and the description thereof. FIG. 18 illustrates further details regarding the vital signs scanner 100. U.S. patent application Ser. No. 12/292,820, filed on May 30, 2014 by Wenyi Zhao et al. and incorporated by reference, further describes the vital signs scanner 100.

Referring now to FIG. 18, a functional block diagram of electronic circuitry 800 within the portable wireless vital signs scanner 100 is shown. The electronic circuitry 800 of the portable wireless vital signs scanner 100 includes a processor 840 at the heart of the system. The processor 840 may be a reduced instruction set processor operating with embedded operating system software. In one embodiment of the invention, the processor is an ARM processor operating with MICRIUM's embedded real time operating system (RTOS).

To provide the wireless communication channels 103A, 103B to a portable device such as a smart phone or a computer tablet, a wireless radio 870 is coupled to the processor 841. The wireless radio 870 is coupled to an antenna 871 that could be internal, as part of an overall radio system, or external to the wireless radio 870. An optional light emitting diode 848, used as a wireless connection indicator, is coupled to the wireless radio to indicate a successful pairing with the personal portable wireless digital multifunction device 104. To scan for vital signs over a period of time such as 10 seconds, the electronic system 800 includes an infrared thermometer 812, an accelerometer 885, a pulse oximetry sensor and a pulse oximetry circuit 880, and analog electrocardiogram circuitry 860. Coupled to the electrocardiogram circuitry 860 is the bottom or top electrode 806B, the front electrode 711, bottom/top electrode connection, and the front electrode connection 806F. As shown in FIG. 1A, a portion of a human body is coupled to the front electrode 711 and the top/bottom electrode 806B to form a circuit.

The pulse oximetry circuit 880 is coupled to a pair of light emitting diodes 808A-808B. Each of these emit light patterns that are reflected off of the user's forehead/temple internally. The reflected light is captured by a photodiode 810 and coupled to the circuit 880. That is, incident light 891 from the light emitting diodes 808A-808B reflects internally off the user's head 116 as reflective light 892 which is received by the photodiode (PD) 810.

The infrared thermometer 812 detects the surface temperature of a use's forehead/temple (or elsewhere) by measuring thermal radiation (referred to as Blackbody radiation) 813 emanating from the head 116 (or other body portion to which the scanner is pressed) of a user.

To power the circuits in the system 800 of the personal portable wireless vital signs scanner 100, a rechargeable battery 850 and a voltage regulator and battery charge controller 854 are coupled together into the circuits in the system 800 when the switch 852 is closed. The battery charge controller 854 is coupled to power pins of a serial connector 856 to receive an external DC voltage supply. The external voltage supply may be used to recharge the battery and power the system 800 when it is connected. The rechargeable battery 850 may hold a charge for a period of seven days, even while scanning multiple times during each day, due to the low power consumption of the circuitry and the limited period of time needed to perform a scan of the vital signs of a user. That is, the vital signs scanner 100 is not expected to be continuously powered on during a day, but powered up periodically to perform the scans as needed.

The processor 840 may include a processor memory 841 to store system instructions to control the circuitry in the system to obtain the scans and process the information obtained through those scans into a proper user format. To store the user data from each of these scans, a nonvolatile memory 844 is coupled to the processor 840. The nonvolatile memory 844 may be soldered to a printed circuit board with the processor 840. In an alternate embodiment of the invention, a connector 845 is provided so that the nonvolatile memory 844 is a removable memory card so that a user's data may be transferred from one scanner to the next, if needed.

A power LED 851 may be coupled to the processor 840 to provide an indication that the electronic system 800 is powered up. The system can be manually shut down via the scanning software application 140 so that the scanner 100 powers off. However, the scanner 100 can also automatically shut off after a predetermined period of time to conserve power and a charge on the rechargeable battery 850. The user then just needs to press the power switch 852, once again, to turn the system back on and scan for vital signs of a user.

The processor 840 includes one or more analog digital convertors 842 in order to receive analog signals from the infrared thermometer 812, accelerometer 885, pulse oximetry circuits 880, and ECG analog circuits 860. Electronic system 800 may further include a stereo microphone 875 consisting of a top microphone 875T and a bottom microphone 875B each coupled to a stereo microphone amplifier 874. The stereo microphone amplifier may have its own analog to digital converter, or the processor's analog digital convertor 842 may be used to convert analog signals into digital signals. For example, an ECG analog signal may be converted into digital signals with the analog digital convertor 842 of the processor. The stereo microphone 875 captures audio signals near the wireless vital signs scanner 100. The accelerometer 885 captures movement of the portable wireless vital signs scanner 100.

The combination of the audio information and the movement information may be utilized to determine the quality of the scanning information being obtained by the vital signs capturing circuitry. For example, the stereo microphone 875 may be used to capture noise from a user talking and plot that on a graph indicating noise spikes, or noise lines 330, such as shown in FIG. 3A. This provides feedback to a user about the quality of the scan at these intervals. The accelerometer 885 and the motion information may be similarly used to make a judgment about the quality of the vital signs scanned information being captured by the vital signs circuitry of the infrared thermometer 812, the pulse oximetry circuits 880, and the ECG analog circuits 860.

The microphones 875 in the portable wireless scanner 120 may also used to capture body sounds such as shown in FIGS. 1E-1F and store the captured body sounds in memory 844 as a potential symptom of a medical condition of the users body. For example, heart beat sounds 155 may be captured by the microphones 875 when the scanner 100 is positioned against skin of the chest 114 near ones heart 156, as is illustrated in FIG. 1E. As another example, lung or breathing of air entering and exiting ones lungs, respiration sounds 157, may be captured by the microphones 875 when the scanner 100 is positioned against skin of the chest 114 near a lung 158 in ones body, as is illustrated in FIG. 1F.

To further optimize scanning results, scan quality algorithm monitor the vita signs scanning process and can provide feedback (visual and/or audible) to the user, such as through the multifunction device 104.

An optional audible sound generator 847 in the scanner 100 may be coupled to the processor 840 to provide audible user feedback to the user during the scanning process. The user feedback may help the user to perform better vital signs scan with the wireless vital signs scanner 100 and acquire a higher quality of vital signs measurements. The audible sound generator 847 may generate alert sounds indicating when the scanning process begins and ends. It may also generate an error signal indicating to the user that he is not properly using the scanner 100 and provide instructions.

CONCLUSION

Various specific materials, designs, dimensions, etc. are provided and are considered highly beneficial embodiments of the present disclosure in one regard. However, in other regards, such specifics are also merely illustrative of broader aspects of the present disclosure and should not be considered necessarily a limit to such broader aspects unless expressly specified to be required. In particular, the various specific dimensions provided as such examples are intended to be about any particular values provided, with typical tolerances and ranges of suitable alternatives as would be apparent to one of ordinary skill. Where particular combinations of such dimensions are provided for exemplary illustration of certain embodiments, the relative relationships between them are also contemplated as having been herein disclosed as additional beneficial aspects (even if the specific values of the relative dimensions change). For example, certain lengths, widths, and/or depths of particular components shown and described for a particular assembly provide overall geometries, which may be varied by changing certain sub-sets of such dimensions, but may also be fixed relative to the ratios of these values despite the values changing (as long as their general relationship remains constant). Similarly, such dimensions of different component parts also have similar relative relationships, which are similarly contemplated, also as apparent to one of ordinary skill.

When implemented in software, the elements of the embodiments of the invention are essentially the code segments or instructions to perform the functional tasks described herein. The code segments or instructions are executable by a processor, such as a signal processor 206 shown in FIG. 2B, and can be stored in a storage device or a processor readable storage medium, such as memory 208, awaiting execution. The processor readable storage medium may include any medium that can store information. Examples of the processor readable storage medium include an electronic circuit, a semiconductor memory device, a read only memory (ROM), a flash memory, an erasable programmable read only memory (EPROM), a floppy diskette, a CD-ROM, an optical disk, a hard disk. The code segments or instructions may be downloaded via computer networks such as the Internet, Intranet, etc. into the processor readable storage medium.

Various combinations and sub-combinations, and modifications as may be made, of the presently disclosed components and embodiments and aspects are contemplated whether or not specifically disclosed herein, to the extent and as would be apparent to one of ordinary skill in the art upon review of this disclosure and in order to suit a particular intended purpose or application.

While certain embodiments of the disclosure have been described, these embodiments have been presented by way of example only, and are not intended to limit the scope of the disclosure. Indeed, the novel methods, systems, and devices described herein may be embodied in a variety of other forms. Furthermore, various omissions, substitutions and changes in the form of the methods, systems, and devices described herein may be made without departing from the spirit of the disclosure. For example, certain features that are described in this specification in the context of separate implementations may also be implemented in combination in a single implementation. Conversely, various features that are described in the context of a single implementation may also be implemented in multiple implementations, separately or in sub-combination. Moreover, although features may be described above as acting in certain combinations and even initially claimed as such, one or more features from a claimed combination may in some cases be excised from the combination, and the claimed combination may be directed to a sub-combination or variations of a sub-combination. Accordingly, the claimed invention is to be limited only by patented claims that follow below.

What is claimed is:

1. A non-invasive method of measuring vital signs with a portable multi-sensor vital signs scanner, the non-invasive method of measuring vital signs comprising:

applying the portable multi-sensor vital signs scanner to a user's body in a first usage configuration for a first measurement period, wherein the first usage configuration includes pressing one electrode of the vital signs scanner with the user's finger while another electrode of the vital sign scanner is pressed against the user's temple;

measuring a plurality of vital signs data with the vital signs scanner in the first usage configuration;

applying the portable multi-sensor vital signs scanner to the user's body in a second usage configuration for a second measurement period, wherein the second usage configuration includes pressing the vital signs scanner against the user's chest;

recording sound using a microphone of the vital signs scanner when the vital signs scanner is in the second usage configuration;

measuring data related to motion of the user's chest using an accelerometer of the vital signs scanner when the vital signs scanner is in the second usage configuration;

providing feedback to the user in response to detecting one or more noise signatures based on the data from the accelerometer, wherein the feedback includes providing an indication to the user to modify at least one of a gripping or a positioning of the vital signs scanner;

using data from the accelerometer to make an initial determination of a respiration rate of the user, the respiration rate including a maximum inhalation time point and a maximum exhalation time point;

determining an alternate maximum inhalation time point and an alternate maximum exhalation time point based on at least the maximum inhalation time point, the maximum exhalation time point, and the recorded sound; and determining a final respiration rate based on at least the maximum inhalation time point, the maximum exhalation time point, the alternate maximum inhalation time point.

2. The non-invasive method of claim 1, further comprising:

signal processing a plurality of sensor signals captured during the first measurement period with a signal processing model to reduce noise and to obtain a value for one or more vital signs.

3. The non-invasive method of claim 1, further comprising:

signal processing the plurality of sensor signals captured during the first measurement period with a first interaction model to correct and improve the vital signs measurement results in response to the user interaction with the vital signs scanner.

4. The non-invasive method of claim 3, further comprising:

comparing the vital signs measurement results with a physiological model to validate the vital signs measurement results.

5. The non-invasive method of claim 1, further comprising:

signal processing a plurality of sensor signals captured during the second measurement period with a second interaction model to correct and improve the vital signs measurement results in response to the user interaction with the vital signs scanner.

6. The non-invasive method of claim 5, further comprising:

comparing the vital signs measurement results with a physiological model to validate the vital signs measurement results.

7. The non-invasive method of claim 1, further comprising:

signal processing a sensor signal captured by a first sensor during the first measurement period with a first signal processing model to reduce noise and to obtain a first value for a vital sign;

signal processing the sensor signal captured by the first sensor during the first measurement period with a second signal processing model to reduce noise and to obtain a second value for the vital sign; and fusing the first value and the second value of the vital sign together to generate a vital sign output value for the vital sign.

8. The non-invasive method of claim 7, wherein the vital sign is pulse width transit time (PWTT).

* * * * *